(12) United States Patent
Kateb et al.

(10) Patent No.: US 9,754,371 B2
(45) Date of Patent: Sep. 5, 2017

(54) MULTI MODALITY BRAIN MAPPING SYSTEM (MBMS) USING ARTIFICIAL INTELLIGENCE AND PATTERN RECOGNITION

(71) Applicant: California Institute of Technology, Pasadena, CA (US)

(72) Inventors: Babak Kateb, Brentwood, CA (US); Shouleh Nikzad, Valencia, CA (US)

(73) Assignees: California Institute of Technology, Pasadena, CA (US); International Brain Mapping and Intra-Operative Surgical Planning Foundation, West Hollywood, CA (US)

( * ) Notice: Subject to any disclaimer, the term of this patent is extended or adjusted under 35 U.S.C. 154(b) by 191 days.

(21) Appl. No.: 14/815,768

(22) Filed: Jul. 31, 2015

(65) Prior Publication Data
US 2016/0035093 A1  Feb. 4, 2016

Related U.S. Application Data

(60) Provisional application No. 62/031,719, filed on Jul. 31, 2014.

(51) Int. Cl.
*G06K 9/00* (2006.01)
*G06T 7/00* (2017.01)
(Continued)

(52) U.S. Cl.
CPC .......... *G06T 7/0014* (2013.01); *A61B 5/0035* (2013.01); *A61B 5/0042* (2013.01);
(Continued)

(58) Field of Classification Search
CPC ...... A61B 34/10; A61B 90/37; G06K 9/0014; G06K 9/00147; G06K 9/6269
See application file for complete search history.

(56) References Cited

U.S. PATENT DOCUMENTS 6,109,270 A * 8/2000 Mah ...................... A61B 5/7264
                                                          128/924
6,718,196 B1   4/2004 Mah et al.
(Continued)

OTHER PUBLICATIONS

Haglund, M. M., et al., "Enhanced Optical Imaging of Human Gliomas and Tumor Margins", Neurosurgery, vol. 38, No. 2, 1996.
(Continued)

*Primary Examiner* — Utpal Shah
(74) *Attorney, Agent, or Firm* — Gates & Cooper LLP

(57) ABSTRACT

A Multimodality Brain Mapping System (MBMS), comprising one or more scopes (e.g., microscopes or endoscopes) coupled to one or more processors, wherein the one or more processors obtain training data from one or more first images and/or first data, wherein one or more abnormal regions and one or more normal regions are identified; receive a second image captured by one or more of the scopes at a later time than the one or more first images and/or first data and/or captured using a different imaging technique; and generate, using machine learning trained using the training data, one or more viewable indicators identifying one or abnormalities in the second image, wherein the one or more viewable indicators are generated in real time as the second image is formed. One or more of the scopes display the one or more viewable indicators on the second image.

20 Claims, 9 Drawing Sheets

(51) Int. Cl.
| | |
|---|---|
| G02B 21/36 | (2006.01) |
| G02B 21/00 | (2006.01) |
| G02B 23/24 | (2006.01) |
| A61B 6/00 | (2006.01) |
| A61B 5/00 | (2006.01) |
| A61B 5/055 | (2006.01) |
| G01R 33/48 | (2006.01) |
| A61B 8/08 | (2006.01) |
| A61B 90/00 | (2016.01) |
| A61B 34/10 | (2016.01) |
| G01R 33/56 | (2006.01) |

(52) U.S. Cl.
CPC .......... *A61B 5/7267* (2013.01); *A61B 6/5247* (2013.01); *A61B 90/37* (2016.02); *G02B 21/0012* (2013.01); *G02B 21/367* (2013.01); *G02B 23/24* (2013.01); *G06K 9/0014* (2013.01); *A61B 5/0084* (2013.01); *A61B 5/055* (2013.01); *A61B 5/4064* (2013.01); *A61B 5/4094* (2013.01); *A61B 5/7203* (2013.01); *A61B 8/5261* (2013.01); *A61B 34/10* (2016.02); *A61B 2090/364* (2016.02); *G01R 33/4808* (2013.01); *G01R 33/5608* (2013.01); *G06K 9/00147* (2013.01); *G06T 2207/10048* (2013.01); *G06T 2207/10081* (2013.01); *G06T 2207/10088* (2013.01); *G06T 2207/10092* (2013.01); *G06T 2207/10132* (2013.01); *G06T 2207/30016* (2013.01)

(56) References Cited

U.S. PATENT DOCUMENTS

| | | | |
|---|---|---|---|
| 2008/0292194 A1* | 11/2008 | Schmidt | G06T 7/0012 382/217 |
| 2010/0198080 A1* | 8/2010 | Liu | A61B 5/0071 600/477 |
| 2010/0260396 A1* | 10/2010 | Brandt | G06K 9/4671 382/131 |
| 2011/0044521 A1* | 2/2011 | Tewfik | G06K 9/6206 382/131 |
| 2013/0085344 A1* | 4/2013 | Merkl | G06F 19/3437 600/300 |
| 2013/0182931 A1* | 7/2013 | Fan | G06T 7/0081 382/131 |
| 2013/0329973 A1 | 12/2013 | Cao et al. | |
| 2014/0161337 A1* | 6/2014 | Raykar | G06T 7/33 382/131 |
| 2016/0005183 A1* | 1/2016 | Thiagarajan | A61B 5/055 382/131 |
| 2017/0020460 A1* | 1/2017 | Leblond | A61B 5/0075 |

OTHER PUBLICATIONS

Poon, W. S., et al., "Laser-induced fluorescence: experimental intraoperative delineation of tumor resection margins", Journal of Neurosurgery 76:679-686, Apr. 1992.

Lin, W.C., et al., "Brain tumor demarcation using optical spectroscopy; an in vitro study", Journal of Biochemical Optics, 5(2), 214-220, Apr. 2000.

Frisoli, J. K., et al., "Pharmacokinetics of a Fluorescent Drug Using Laser-Induced Fluorescence", Cancer Research 53, 5954-5961, Dec. 15, 1993.

Tsai, J.C., et al., "Flurospectral Study of the Rat Brain and Glioma in Vivo", Lasers in Surgery and Medicine 13:321-331 (1993).

Papaioannou, T., et al., "Thermal imaging of brain tumors in a rat glioma model", SPIE proceedings, vol. 4615, Biomedical Diagnostic, Guidance, and Surgical-Assist Systems IV, San Jose CA, 2002, oral/poster presentation.

Thompson, R. C., et al., "Detection of experimental brain tumors using time-resolved laser-induced fluorescence spectroscopy", Proc. SPIE vol. 4613, pp. 8-12, Optical Biopsy IV (Robert R. Alfano, Editor), San Jose CA, 2002.

Bottiroli, G., et al., "Brain Tissue Autofluorescence: An Aid for Intraoperative Delineation of Tumor Resection Margins", Cancer Detection & Prevention, vol. 22, Issue 4, pp. 330-339, 1998.

Burger, P. C., et al., "Topographic anatomy and CT correlations in the untreated glioblastoma multiforme", Journal of Neurosurgery 68:698-704, May 1988.

Chung, Y. G., et al., "Diagnostic Potential of Laser-Induced Autofluorescence Emission in Brain Tissue", Journal of Korean Medical Science 12:135-142, 1997.

Sciskowski, P. W., et al., "Biochemical Characterization of Three Hamster Melanoma Variants—II, Glycolysis and Oxygen Consumption", International Journal of Biochemistry 16(3): 327-31, 1984.

Halaban, R., "Pigmentation in Melanomas: Changes Manifesting Underlying Oncogenic and Metabolic Cctivities", Oncology Research/Anti-Cancer Drug Design 13(1): 3-8, 2002.

Comaniciu, D., "Mean Shift: A Robust Approach Toward Feature Space Analysis", IEEE Trans. Pattern Anal. Machine Intell., vol. 24, No. 5, pp. 603-619, May 2002.

Meer, P., "Edge Detection with Embedded Confidence", IEEE Trans. Pattern Anal. Machine Intell., vol. 23, No. 12, pp. 1351-1365, Dec. 2001.

Muller, B., et al., "Neural Networks—an Introduction", Springer, Berlin Heidelberg New York, Computer Physics Communications 67, pp. 357-359, 1991, North-Holland.

Hopfield, J. J., "Neural networks and physical systems with emergent collective computational abilities", Proc. Natl. Acad. Sci. USA, vol. 79, pp. 2554-2558, Apr. 1982, Biophysics.

Rumelhart, D. E., et al., "Learning representations by back-propagating errors", Nature, vol. 323, No. 9, pp. 533-536, Oct. 1986.

Rumelhart, D. E., et al., "Learning Internal Representations by Error Propagation", In D. E. Rumelhart and J. L. McClelland (Eds.), MIT Press, Cambridge, Parallel Distributed Processing, vol. 1, Chapter 8, pp. 318-363, 1986.

Kanter, I., et al., "Associative recall of memory without errors", Phys Rev A, vol. 35, No. 1, pp. 380-392, Jan. 1, 1987.

Laws, E. R., et al., "Surgical Management of Intracranial Gliomas—Does Radical Resection Improve Outcome?", Acta Neurochirurgica Supplement, vol. 85, pp. 47-53, 2003.

Brugge, J. F., et al., "Thermal images of somatic sensory cortex obtained through the skull of rat and gerbil", Exp Brain Res. 1995;106(1):7-18.

George, J. S., et al., "IR thermal imaging of a monkey's head: local temperature changes in response to somatosensory stimulation", Adv Exp Med Biol. 1993;333:125-36.

Zhou, J., et al., "Extraction of Brain Tumor from MR Images Using One-Class Support Vector Machine", in: IEEE Conf. on Engineering in Medicine and Biology, 2005, pp. 6411-6414.

Schmidt, M., et al., "Segmenting Brain Tumors using Alignment-Based Features", in: IEEE Internat. Conf. on Machine learning and Applications, 2005, pp. 215-220.

Lefohn, A. E., et al., "Interactive, GPU-based Level Sets for 3D Segmentation", Technical Report, University of Utah, R. E. Ellis and T. M. Peters (Eds.): MICCAI 2003, LNCS 2878, pp. 564-572, 2003.

Zhu, Y., et al., "Computerized Tumor Boundary Detection Using a Hopfield Neural Network", IEEE Transactions on Medical Imaging 16 (1) (1997), pp. 55-67.

Xu, C., et al., "Snakes, Shapes, and Gradient Vector Flow", IEEE Transactions on Image Processing, 7(3), pp. 359-369, Mar. 1998.

Xu, C., et al., "Gradient Vector Flower: A New External Force for Snakes", Proc. IEEE Conf. on Comp. Vis. Patt. Recog. (CVPR), Los Alamitos: Comp. Soc. Press, pp. 66-71, Jun. 1997.

Xu, C., et al., "Global Optimality of Gradient Vector Flow", Proc. of 34th Annual Conference on Information Sciences and Systems (CISS'00), Princeton University, Mar. 15-17, 2000.

Li, H. D., et al., "Markov Random Field for Tumor Detection in Digital Mammography", IEEE Transactions on Medical Imaging, vol. 14, No. 3, pp. 565-576, Sep. 1995.

(56) References Cited

OTHER PUBLICATIONS

Lee, C.H., et al., "Segmenting Brain Tumors with Conditional Random Fields and Support Vector Machines", CVBIA 2005, Lecture Notes in Computer Science, vol. 3765, pp. 469-478, 2005.
Sturm, P. F., et al., "On Plane-Based Camera Calibration: A General Algorithm, Singularities, Applications", CVPR'99, Nov. 18, 2015.
Clarke, T. A., et al., "The Development of Camera Calibration Methods and Models", Photogrammetric Record, 16(91): 51-66, Apr. 1998.
Somayajula, S., et al., "Mutual Information Based Non-Rigid Mouse Registration Using a Scale-Space Approach", Proc. of ISBI, pp. 1147-1150, May 2008.
Tan, T. C., et al., "Image Guided Craniotomy for Cerebral Metastases: Techniques and Outcomes", Neurosurgery, vol. 53, No. 1, pp. 82-90, Jul. 2003.
Black, P. McL., et al., "Development and Implementation of Intraoperative Magnetic Resonance Imaging and its Neurosurgical Applications", Neurosurgery, vol. 41, No. 4, pp. 831-842, Oct. 1997.
Byrne, T. N., et al., "Brain metastasis from melanoma", J. Neuro. Oncol. 1, pp. 313-317, 1983.
Gorbach, A. M., "Infrared Imaging of Brain Function", Advances in Experimental Medicine and Biology Journal, vol. 333, pp. 95-123, 1993.
Gorbach, A. M., et al., "Intraoperative infrared imaging of brain tumors", J. Neurosurg., vol. 101, pp. 960-969, Dec. 2004.
Ecker, R. D., "Vision of the future: Initial experience with intraoperative real-time high-resolution dynamic infrared imaging", Journal of Neurosurgery, vol. 97 (6): 1460-71, Dec. 2002.
Arora, N., et al., "Effectiveness of a noninvasive digital infrared thermal imaging system in the detection of breast cancer", The American Journal of Surgery, 196(4):523-6, 2008.
Black, P., et al., "Development and Implementation of Intraoperative Magnetic Resonance Imaging and Its Neurosurgical Applications", Neurosurgery, vol. 41:831-845, Oct. 1997.
Deangelis, L. M., "Brain Tumors", The New England Journal of Medicine, vol. 344, No. 2, pp. 114-123, Jan. 11, 2001.
Di Carlo, A., et al., "Thermography and the Possibilities for Its Applications in Clinical and Experimental Dermatology", Clinics in Dermatology 13:329:336, (1995).
Fahlbusch, R., et al., "A Review of Cranial Imaging Techniques: Potential and Limitations", Clinical Neurosurgery, The Congress of Neurological Surgeons, vol. 54, ch17, 100-104, (2007).
Frangioni, J. V., "New Technologies for Human Cancer Imaging", Journal of Clinical Oncology, vol. 26, No. 24, pp. 4012-4021, Aug. 20, 2008.
Gonzalez, F. J., "Infrared Imager Requirements for Breast Cancer Detection", Proceedings of the 29th Annual Int'l Conference of the IEEE EMBS, Cite Internationale, Lyon, France, pp. 3312-3314, Aug. 23-26, 2007.
Gorbach, A., et al., "Objective, Real-Time, Intraoperative Assessment of Renal Perfusion Using Infrared Imaging", American Journal of Transplantation;3(8):988-93, (2003).
Gorbach, A. M., et al., "Assessment of Critical Renal Ischemia With Real-Time Infrared Imaging", Journal of Surgical Research 149(2):310-318, (2008).
Hadani, M., et al., "Novel, Compact, Intraoperative Magnetic Resonance Imaging-Guided System for Conventional Neurosurgical Operating Rooms", Neurosurgery, vol. 48, No. 4, pp. 799-809, Apr. 2001.
Hall, W., et. al., "Safety, Efficacy, and Functionality of High-Field Strength Interventional Magnetic Resonance Imaging for Neurosurgery", Neurosurgery, vol. 46(3), pp. 632-642, Mar. 2000.
Hall, W. A., et al., "Intraoperative MR-Guided Neurosurgery", Journal of Magnetic Resonance Imaging 27 (2):368-375, Feb. 2008.
Head, J. F., et al., "The Important Role of Infrared Imaging in Breast Cancer", IEEE Eng Med Biol Mag. 19(2) 52-57, May/Jun. 2000.
Hill, D., et al., "Measurement of Intraoperative Brain Surface Deformation under a Craniotomy", Neurosurgery, vol. 43(3), pp. 514-526, Sep. 1998.
Holland, B. A., et al., "Magnetic Resonance Imaging of Primary Intracranial Tumors: a Review", International Journal of Radiation Oncology, Biology, Physics, vol. 11, pp. 315-321, 1985.
Jiang, L. J., et al., "A perspective on medical infrared imaging", Journal of Medical Engineering & Technology, vol. 29, No. 6, pp. 257-267, Nov./Dec. 2005.
Knauth, M., et al., "Intraoperative MR Imaging Increases the Extent of Tumor Resection in Patients with High-Grade Gliomas", Am J Neuroradiology 20(9):1642-1646, Oct. 1999.
Kelly, P. J., et al., "Stereotactic Histologic Correlations of Computed Tomography—and Magnetic Resonance Imaging-Defined Abnormalities in Patients with Glial Neoplasms", Mayo Clinic Proceeding 62:450-459, 1987.
Konerding, M. A., "Impact of Fibroblast Growth Factor-2 on Tumor Microvascular Architecture—A Tridimensional Morphometric Study", American Journal of Pathology, vol. 152, No. 6, pp. 1607-1616, Jun. 1998.
Lindner, D., et al., "Application of Intraoperative 3D Ultrasound During Navigated Tumor Resection", Minim Invasive Neurosurg 49(4):197-202, (2006).
McCulloch, J., "Perivascular nerve fibres and the cerebral circulation", Trends in Neurosciences, vol. 7, No. 5, pp. 135-138, May 1984.
McGirt, M. J., et al., "Independent association of extent of resection with survival in patients with malignant brain astrocytoma", J Neurosurg., vol. 110(1), pp. 156-162, Jan. 2009.
Merla, A., "Functional Infrared Imaging in Medicine: A Quantitative Diagnostic Approach", Conf Proc IEEE Eng Med Biol Soc. 1:224-7 Aug. 30-Sep. 3, 2006.
Michel, U., et al., "Infrared thermography in malignant melanoma—Diagnostic potential and limits", [in German], Hautarzt 36:83-89, (1985).
Mineo, J. F., et al., "Glioblastomas: clinical study and search for prognostic factors", [in French], Neurochirurgie, 48:500-509, 2002.
Mital, M., et al., "Thermal Detection of Embedded Tumors Using Infrared Imaging", J Biomech Eng., vol. 129, pp. 33-39, Feb. 2007.
Mitchell, P., et al., "Surgery for malignant gliomas: mechanistic reasoning and slippery statistics", Lancet Neurology, vol. 4, pp. 413-422, 2005.
Mittal, S., et al., "Intraoperative magnetic resonance imaging in neurosurgery: the Brigham concept", Acta Neurochir Suppl. 2006;98:77-86, (2006).
Nabavi, A., et al., "Serial Intraoperative Magnetic Resonance Imaging of Brain Shift", Neurosurgery, vol. 48, No. 4, pp. 787-797, Apr. 2001.
Nakagawa, A., et al., "Intraoperative infrared brain surface blood flow monitoring during superficial temporal artery-middle cerebral artery anastomosis in patients with childhood moyamoya disease", Childs Nerv Syst 24(11):1299-305, 2008.
Nakao, N., "Updating of Neuronavigation Based on Images Intraoperatively Acquired with a Mobile Computerized Tomographic Scanner: Technical Note", Minim Invasive Neurosurg; 46(2):117-120, 2003.
Nazzaro, J. M., "The role of surgery in the management of supratentorial intermediate and high-grade astrocytomas in adults", Journal of Neurosurgery 73:331-344, 1990.
Nishikawa, K., et al., "Intraoperative Thermal Imaging in Esophageal Replacement: Its Use in the Assessment of Gastric Tube Viability", Surg Today 36(9):802-806, 2006.
Rasmussen Jr, I. A., et al., "Functional neuronavigation combined with intra-operative 3D ultrasound: Initial experiences during surgical resections close to eloquent brain areas and future directions in automatic brain shift compensation of preoperative data", Acta Neurochir (Wien) 149: 365-378, 2007.
Reinertsen, I., et al., "Validation of vessel-based registration for correction of brain shift", Medical Image Analysis 11(4):374-88, 2007.
Samaras, C. A., et al., "The Role of Thermography in Breast Cancer", Contemporary Surgery, vol. 23, pp. 31-38, Apr. 1983.
Sanai, N., et al., "Glioma Extent of Resection and Its Impact on Patient Outcome", Neurosurgery, vol. 62, No. 4, pp. 753-766, Apr. 2008.

(56) References Cited

OTHER PUBLICATIONS

Saxena, A. K., et al., "Infrared Thermography: Experience from a decade of Pediatric Imaging", Eur J Pediatr, 167: 757-764, 2008.
Schulder, M., et al., "Cranial surgery navigation aided by a compact intraoperative magnetic resonance imager", J Neurosurg 94:936-945, 2001.
Schulder, M., et al., "Intraoperative Magnetic Resonance Imaging: Impact on Brain Tumor Surgery", Cancer Control, vol. 10, No. 2, pp. 115-124, Apr. 2003.
Shevelev, I. A., et al., "Thermoimaging of the brain", Journal of Neuroscience Methods 46, pp. 49-57, 1993.
Shevelev, I. A., "Functional Imaging of the Brain by Infrared Radiation (Thermoencephaloscopy)". Progress in Neurobiology, vol. 56, pp. 269-305, 1998.
Shevelev, I. A., "Temperature Topography of the Brain Cortex: Thermoencephaloscopy",Brain Topography, vol. 5, No. 2, pp. 77-85, 1992.
Shi, W. M., et al., "Volumetric measurement of brain tumors from MR imaging", Journal of Neuro-Oncology 37:87-93, 1998.
Stupp, R., et al., "Radiotherapy plus Concomitant and Adjuvant Temozolomide for Glioblastoma", N Engl J Med. 352;10, pp. 987-996, Mar. 10, 2006.
Tempany, C. M. C., et al., "Advances in Biomedical Imaging", JAMA 285(5):562-567, 2001.
Unsgaard, G., et al., "Intra-operative 3D ultrasound in neurosurgery", Acta Neurochir (Wien) 148(3):235-53, 2006.
Ueda, M., et al., "Localisation of Sensory Motor Cortex During Surgery by Changes of Cortical Surface Temperature after Median Nerve Stimulation", The Lancet, vol. 350, No. 9077, p. 561, Aug. 23, 1997.
Patterson, H., "Nobody can Afford a Brain Tumor: The Financial Impact of Brain Tumors on Patients and Families. A Summary of Findings", NBT Foundation San Francisco, CA, May 2007. http://www.sehn.org/tccpdf/brain%20tumor%20financial%20impact.pdf.
Nathoo, N., et al., "Metastases to the brain: current management perspectives", Expert Rev. Neurotherapeutics 4(4), pp. 633-640, 2004.
Barrett, A. H., et al., "Microwave Thermography in the Detection of Breast Cancer", AJR, Am J Roengenol 34(2);365-368, 1980.
Frieboes, H. B., et al., "Computer simulation of glioma growth and morphology", NeuroImage, vol. 37, 2007, S59-S70.
Kateb, B., et al., "Infrared thermal imaging:A review of the literature and case report", NeuroImage, vol. 47, 2009, T154-T162.
Sanga, S., et al., "Predictive oncology: A review of multidisciplinary, multiscale in silico modeling linking phenotype, morphology and growth", NeuroImage, vol. 37, 2007, S120-S134.
International Preliminary Report on Patentability (including the Search Report) dated Feb. 9, 2017 for PCT Application No. PCT/US15/43309 filed on Jul. 31, 2015.

* cited by examiner

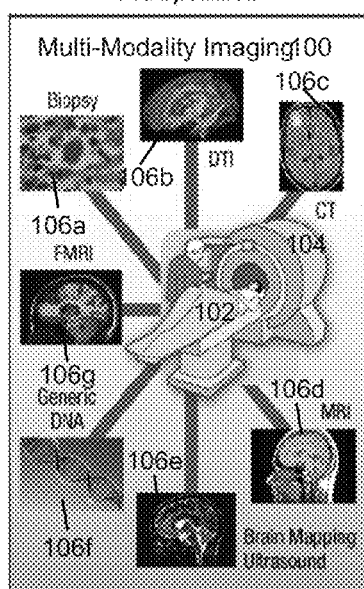
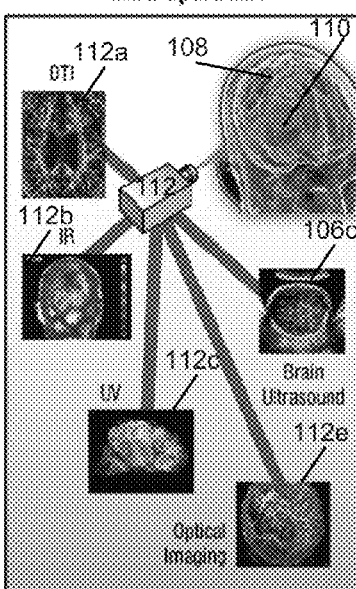
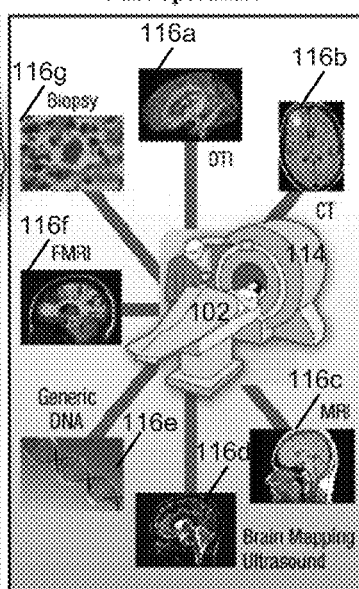
FIG. 1A  FIG. 1B  FIG. 1C  FIG. 1D  FIG. 1E

US 9,754,371 B2

MULTI MODALITY BRAIN MAPPING SYSTEM (MBMS) USING ARTIFICIAL INTELLIGENCE AND PATTERN RECOGNITION

CROSS-REFERENCE TO RELATED APPLICATIONS

This application claims the benefit under 35 U.S.C. Section 119(e) of the following co-pending and commonly-assigned U.S. provisional patent application(s), which is/are incorporated by reference herein:

Provisional Application Ser. No. 62/031,719, filed on Jul. 31, 2014, by Shouleh Nikzad and Babak Kateb, entitled "SMART MICROSCOPE AND ENDOSCOPES USING MULTIMODAL IMAGING, ARTIFICIAL INTELLIGENCE AND PATTERN RECOGNITION,".

STATEMENT REGARDING FEDERALLY SPONSORED RESEARCH AND DEVELOPMENT

The invention described herein was made in the performance of work under a NASA contract, and is subject to the provisions of Public Law 96-517 (35 USC 202) in which the Contractor has elected to retain title.

BACKGROUND OF THE INVENTION

1. Field of the Invention

The present invention relates generally to a medical imaging technique.

2. Description of the Related Art (Note: This application references a number of different publications as indicated throughout the specification by reference numbers enclosed in brackets, e.g., [x]. A list of these different publications ordered according to these reference numbers can be found below in the section entitled "References." Each of these publications is incorporated by reference herein.)

The incidence of brain tumors, including metastasis, is on the rise. Despite considerable advances in diagnosis and treatment, the survival rate of patients with malignant brain tumors has not significantly improved. The mortality from malignant brain tumors remains high, as the median survival rate is 12 to 18 months in patients with glioblastoma and 41 months in patients with anaplastic astrocytomas [60, 88, 108, 114]. Currently, brain tumors are treated through chemotherapy, immunotherapy and surgery. Surgical resection followed by radiotherapy and chemotherapy offers a survival benefit, particularly when resection is complete [80, 86, 88, 94, 100]. Thus, surgical resection provides significant benefit should surgeons achieve near complete resection, and therefore the completeness of removal of the tumor is a major factor in improving survival and quality of life in tumor patients.

Although many advances have been made in the field of brain imaging in the last decades, brain shift, also known as post-imaging brain distortion, often makes intraoperative delineation of the tumors difficult, as its preoperative imaging can no longer be fully relied on [74, 77, 90, 98]. Moreover, it is difficult to distinguish brain tumors from normal surrounding tissue if they exhibit an infiltrative nature, which makes it virtually impossible to achieve near total resection.

Therefore, there is a great need for development of new imaging techniques and integration of multimodality imaging (pre-, intra-, and post-operative imaging, and endoscopic imaging) with advanced mathematical pattern recognition/predictive modeling as well as parallel computing and supercomputing for data analysis. One or more embodiments of the invention can satisfy this need by integrating various imaging technologies (including intra-operative brain imaging/mapping technologies such as thermography, Ultraviolet (UV) imaging, Magnetic Resonance Imaging (MRI), and Computed Tomography (CT)) with an intelligent system (including machine learning), to provide a real time intra-operative tool that delineates abnormal cells from normal cells.

SUMMARY OF THE INVENTION

One or more embodiments of the invention disclose a method and apparatus comprising machine learning that uses shared data and/or predictive modeling to identify and/or predict abnormal growth in (e.g., microscope/endoscope) images. The system can comprise a smart microscope and/or endoscope using multimodal imaging, artificial intelligence (AI), and pattern recognition. A system according to one or more embodiments can comprise one or more scopes (e.g., including an optical scope) coupled to one or more processors, wherein the one or more processors obtain training data from one or more first images, wherein one or more abnormal regions and one or more normal regions are identified; receive a second image (e.g., an optical image) captured by one or more of the scopes at a later time than the one or more first images and/or captured using a different imaging technique; and generate, using machine learning trained using the training data, one or more viewable indicators identifying one or more abnormalities in the second image, wherein the one or more viewable indicators are generated in real time as the second image is formed. One or more of the scopes can display the one or more viewable indicators on the second image. The one or more scopes can comprise, but are not limited to, one or more microscopes, one or more endoscopes, one or more cameras, and/or one or more instruments used to image (e.g., using optical or other wavelengths, as used in medical imaging systems). The system can comprise a Multimodality Brain Mapping System (MBMS) (e.g., obtaining IR, UV, MRI, CT, Ultrasound, or other images, and/or molecular data, cellular data, genomic data, and patient medical data).

One or more of the processors can comprise one or more multi-modality image processors that register at least two of the first images obtained from biopsy, Infrared Imaging, Ultraviolet Imaging, Diffusion Tensor Imaging (DTI), Computed Tomography (CT), Magnetic Resonance Imaging (MRI), Brain Mapping Ultrasound, Generic DNA sequencing, optical imaging, and Functional MRI (FMRI), to form a registered image. One or more of the processors can receive input that identifies or marks the one or more abnormal and normal regions in the registered image.

One or more first images can comprise a pre-operative image and/or an intra-operative image and/or a post operative image of one or more patients.

Cloud and/or parallel computing can be used to connect scopes so that the scopes can access, share, and learn from the data obtained from different scopes. A multi-central parallel computing and machine learning apparatus can be provided. For example, the scopes can comprise one or more first scopes capturing the one or more first images of one or more patients and a second scope capturing the second image of a different patient. The system can further comprise a cloud and/or supercomputing/parallel computing system wherein the training data obtained from the one or more first images captured in the one or more first scopes is shared so that the machine learning learns from the training data to identify the one or more abnormalities in the second image of the different patient.

The processors can predict growth of the one or more abnormalities in the second image from predictive modeling of, and/or pattern recognition in, the training data. One or more of the processors can represent the abnormal regions with first feature vectors defining first coordinates in a feature space; represent the normal regions with second feature vectors defining second coordinates in the feature space, wherein the feature space is selected such that at least some of the first coordinates and at least some of the second coordinates are on opposite sides of a hyper-plane in the feature space; map an image region of the second image to one or more image coordinates in the feature space; classify one or more of the image coordinates as one or more abnormal coordinates depending on one or more factors. The factors can include which side of the hyper-plane the one or more image coordinates lie; and/or proximity of the one or more image coordinates to the first coordinates and/or the hyper-plane. The processors can indicate the image region as an abnormal image region if the image region is mapped to one or more of the abnormal coordinates according to the map. The one or more processors can implement a support vector machine.

One or more embodiments of the invention can be applied during surgical procedures. Since real time intra-operative mapping of brain cancer and epileptic areas is critical in removing the abnormal tissue and leaving the healthy tissue intact, there is a great need for the multimodality intra-operative optical imaging technology according to one or more embodiments of the invention. One or more embodiments of the invention can be implemented in a microscope/endoscope and focus on intra-operative detection of diseased tissue in real time using multimodality imaging data while helping the microscope/endoscope train itself (become more intelligent) and use pattern recognition software to predict the pattern of abnormal (e.g., cancer) growth.

BRIEF DESCRIPTION OF THE DRAWINGS

Referring now to the drawings in which like reference numbers represent corresponding parts throughout:

FIG. 1A-FIG. 1E illustrate an imaging system that uses machine learning, according to one or more embodiments of the invention;

DETAILED DESCRIPTION OF THE PREFERRED EMBODIMENTS

Figure 2:
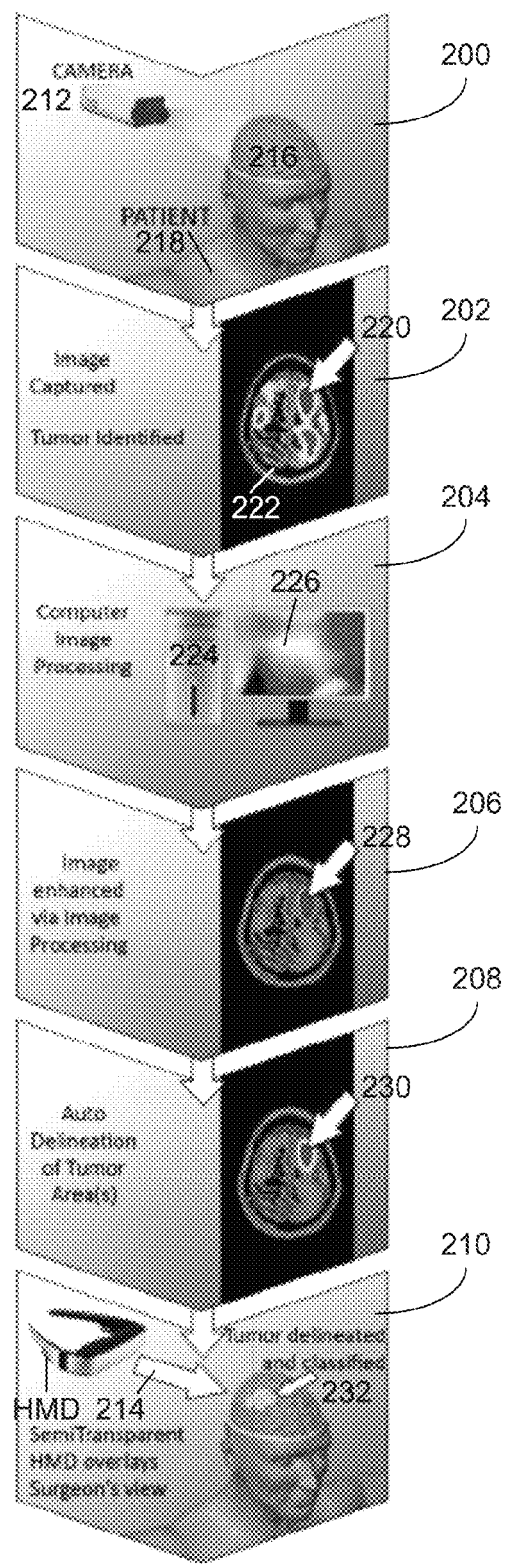
FIG. 2 illustrates a method of imaging according to one or more embodiments of the invention.

In the following description, reference is made to the accompanying drawings which form a part hereof, and which is shown, by way of illustration, several embodiments of the present invention. It is understood that other embodiments may be utilized and structural changes may be made without departing from the scope of the present invention.

One or more embodiments of the invention integrate various imaging technologies to provide a real time intraoperative tool that delineates abnormal cells from normal cells. Real time data analysis using artificial intelligence (AI) and mathematical modeling can be used for pattern recognition so that in a crowded imaging scene, areas of interest can be identified, zoomed in and used during surgery.

One or more embodiments of the invention provide a smart microscope/endoscope similar to current intra-operative microscopes in terms of the visible optics, but further comprising an enhanced multispectral array enabling analysis of the different light spectrums (in real time), which could be analyzed by mathematical/predictive modeling systems using computing systems. The data obtained from the different light spectrums can be integrated with pre-operative images (obtained from Computed Tomography (CT), UV, IR, Magnetic Resonance Imaging (MRI), Ultrasound, etc.,) and pathology report(s) (e.g., histopathology report(s)). The artificial intelligence part of the microscope helps the technology to learn from each case and teach itself using the imaging (pre-, intra-, as well as post-operative imaging), while using mathematical modeling and/or method(s)/system(s) to predict the pattern of abnormal/epileptic region growth.

In one or more embodiments, the multi-modality imaging system includes visualization, registration, and integration of Infrared Thermal Imaging (ITI), UV, visible images, MRI, and biopsy, to provide observers/operators (e.g., neurosurgeons) with a more comprehensive set of data, thus facilitating a more objective decision-making process. The imaging system can be enhanced by auto-delineating tumor resection margins using a semi-supervised learning method/system. The semi-supervised learning method/system can be trained on a manually delineated reference dataset prepared by experts, and then applied in real-time to intraoperative and visual imagery, to (semi-)automatically generate delineations of the resection margins. Giving such valuable real-time information to the surgeon/observer can significantly improve the surgical accuracy and thus contribute significantly to the survival and quality of life of patients with malignant brain tumors (or other tumors).

FIG. 1A-FIG. 1E illustrate a method and system for imaging using machine learning, according to one or more embodiments of the invention.

FIG. 1A illustrates capturing one or more pre-operation images (e.g., multi-modality imaging 100) of tissue (e.g., the brain) in a patient 102 using one or more imaging systems 104. The imaging system(s) 104 can include one or more of the following: biopsy to obtain a biopsy image 106a, Diffusion Tensor Imaging (DTI) to obtain DTI image 106b, CT imaging to obtain a CT image 106c, MRI to obtain an MRI image 106*d*, Brain Mapping Ultrasound to obtain a Brain Mapping Ultrasound image 106*e*, molecular and cellular/genomic data 106*f*, and Functional MRI (FMRI) to obtain an FMRI image 106*g*. Thus, multi-modality imaging can be performed.

FIG. 1B represents capturing one or more intra-operation images of the tissue 108 (e.g., the brain, e.g., the same tissue as imaged in FIG. 1A, or different tissue as compared to the tissue imaged in FIG. 1A) including a diseased/abnormal region 110 (e.g., a cancerous tumor) using one or more imaging systems/cameras 112. The patient in FIG. 1B can be the same patient as in FIG. 1A, or a different patient. The imaging system(s) 112 can include one or more of the following: DTI to obtain a DTI image 112*a*, Infrared (IR) imaging to obtain an IR image 112*b*, Ultraviolet (UV) imaging to obtain a UV image 112*c*, optical imaging to obtain an optical image 112*d*, and brain ultrasound to obtain a brain ultrasound image 112*e*. Thus, multi-modality imaging can be performed and data could be obtained and analyzed using a computing system.

FIG. 1C represents capturing one or more post-operation images (e.g., post previous surgery, post-current surgery) of tissue (e.g., the brain, e.g., the same tissue as imaged in FIG. 1A, or different tissue as compared to the tissue imaged in FIG. 1A and FIG. 1B) in the patient 102 using one or more imaging systems 114. The patient 102 can be the same as the patient(s) in FIG. 1A or FIG. 1B, or a different patient. The imaging system(s) 114 can include one or more of the following: DTI obtaining DTI image 116*a*, CT obtaining CT image 116*b*, MRI obtaining MRI image 116*c*, Brain Mapping Ultrasound obtaining Brain Mapping Ultrasound image 116*d*, Generic DNA sequencing obtaining generic DNA sequencing image 116*e*, and FMRI obtaining FMRI image 116*f*, and biopsy obtaining biopsy image 116*g*. Thus, multi-modality imaging can be performed.

FIG. 1D represents performing a classification using a machine learning system/classifier 118, wherein one or more of the pre-operation images 106*a*-*g*, intra-operation images 112*a*-*e*, and post operation images 116*a*-*g* are combined/registered (e.g., using image processing) and are used to train the machine learning system 118 operating in a training mode 120, thereby obtaining a trained support vector machine 122. The trained support vector machine 122 used in an operation mode 124 classifies tumor and non-tumor tissues in microscope image data and outputs the classification information 126 (e.g., so that tumor regions in the images 112*a*-112*e* obtained during the intra-operation imaging illustrated in FIG. 1B can be identified). The machine learning system 118 can use predictive modeling to identify/predict a pattern of abnormal (e.g., cancer) growth in images captured by microscopes.

FIG. 1E illustrates improving the machine learning technology. For example, the machine learning 118 can further use Hidden Markov, Adaptive Boosting (ADABOOST), or other machine learning technologies 128 to obtain more accurate results 130 for the classification 126 of the tumor and non-tumor tissues during the operation mode 124. The results 130 can be compared 132 to post surgical expert delineations 134 of the abnormal regions in the tissue (e.g., by a medical care provider, using images obtained using the imaging in FIG. 1C) to evaluate accuracy 136 of the results 130. The expert delineations can be provided for the same regions of tissue as classified in 126, or for different tissues obtained from different patients. The evaluation 136 can comprise generating receiver operating characteristic (ROC) curves and comparing the ROC curves for different estimators. The evaluation 136 can comprise performing cross validation. The results of the accuracy evaluation 136 can be used to obtain an improved machine learning technology 138 so that more accurate classification 126 of diseased regions (e.g., in the intra-operation images 112*a*-*e*) by the machine learning is achieved.

Current microscope/endoscope technologies only rely on high resolution visible light with potential integration of few intraoperative imaging technologies. The technology according to one or more embodiments of the invention, on the other hand, can use and combine multiple photonics imaging technologies, standard pre-operative imaging such as MRI, CT, PET, and ultrasound, biopsy, and patient record(s) with real time neurophotonic data, and link the data obtained using these technologies to/using a machine learning technology, as well as mathematical software, which could calculate and predict patterns.

Surgical Setup

In one embodiment, the usual surgical pre-planning procedure does not need to be modified, although (e.g., 60 seconds of) thermal images (as an example of one of the modalities) pre-intra and post-tumor resection can be recorded if necessary. A camera/intraoperative imaging system could be used independently and or used as an integrated part of the intraoperative microscope/endoscope, thereby allowing convenient optical and non-optical (e.g., cellular, molecular, and genomic) access to the operative field. The camera, except for the lens, can be covered with conventional surgical draping to maintain the sterility of the operative site. To reach the proper operating temperature of the detector, an electrical cooler within the camera can be activated (e.g., 20 minutes before taking measurements). The surgical lights near the operative site can be redirected from the surgical field during multi modality measurements (i.e., infrared, UV, etc.), so that they do not affect the infrared measured heat pattern. Sequential digital images can also be obtained during surgery.

Data Acquisition

FIG. 2 illustrates a process of data acquisition, comprising steps 200-210, according to one or more embodiments of the invention.

Blocks 200 and 210 represent capturing one or more images (e.g., using a camera 212, e.g., IR or UV camera and or other multi-modal imaging systems/imaging as illustrated in FIG. 1B) and visual images 214 (e.g., using a head mounted display (HMD), such as glasses, worn by a surgeon/surgical loops), respectively, after the surgical site has been exposed (e.g., when the craniotomy is finished and the brain 216 of the patient 218 has been exposed). Several images and image/data sets can be obtained as the surgeon(s) (e.g., neurosurgeon(s)) proceed with the dissection of the tissue (e.g., brain abnormalities such as brain tumor, Arteriovenous malformation (AVM), epileptic area(s), etc.).

Block 202 represents identifying the abnormal region (e.g., tumor, cancer, an epileptic region treated by intraoperative epilepsy surgery, Arteriovenous malformation (AVM)) 220 in the image 222 captured by camera 212. The step can include human (e.g., pathologist, neurosurgeon) or AI expert delineations delineating the tumor 220 in the image 222. The annotation, delineations, and marking (e.g., of areas for biopsies) can be entered and accessed from a database.

Block 204 represents image processing the captured image 222 using a computer 224 (e.g., in an image processor of the computer 224) to form a processed image 226. The image processing can comprise image registration.

Block 206 represents enhancing/manipulating the processed image 226 via image processing (in an image processor), e.g., to improve brightness, color, contrast, etc., to form an enhanced image 228. In one or more embodiments, a Red Hat Linux™ software package can be used for the image processing.

Block 208 represents performing auto-delineation 230 of the tumor area (e.g., in a machine learning processor), using a supervised learning technique trained using the enhanced image 226 comprising the AI expert delineations (e.g., accessed from the database) with possibility of override by human operator. The automatic delineation can be performed by a computer/AI system. New data can also be integrated into the supervised training delineation tool.

Block 210 represents enhancing the surgeon's view 216 using the semi-transparent HMD that overlays the auto-delineation 230 and classification of the abnormality 232 on the surgeon's view 214.

Thermal imaging can also be performed after completion of the surgical procedure. For example, when the tumor is believed to have been completely removed, Intraoperative Brain Mapping (i.e., thermal, UV imaging, and/or other imaging) of the cavity can be performed, e.g., for 60-120 seconds, followed by auto-delineation based on the result. For those areas suspected of harboring residual tumor tissue, several options can be exercised, including, but not limited to, (1) resecting and separately analyzing those residual areas that correspond to abnormal tissue, (2) performing biopsy only on those volumes felt to represent a tumor by temperature criteria alone, and (3) abstaining from sampling those areas suspected of being tumor, but residing in critical brain areas, so as not to jeopardize the safety of the surgical procedure.

Multimodality Intraoperative Brain Mapping (i.e., thermal, UV, and/or other images or data) can be compared with the stereotactic images, with pathology reports generated throughout all the phases of the operative procedure, and with pre-intra and post-operative MRI and CT scans and other datasets (e.g., cellular, molecular, and genomic data).

In one or more embodiments, IR images can be captured using a low-resolution Thermal imaging technologies. For example, the paper published by Kateb et. al [123] describes a thermal imaging system (with a 320×240 pixel size, a thermal response in the IR wavelength band of 7.5-13.5 micrometers, and having a sensitivity of less than 0.1° C.). The auto-delineation system according to one or more embodiments of the invention can be rapidly implemented using thermal image(s) captured in the thermal imaging system described in [123] or an advanced NASA/JPL IR system. In one or more embodiments, the thermal image data from a thermal camera (e.g., a thermal imaging system that is currently commercially available) can be accessed via its firewire interface, the IR imagery can be stored on a computer interfacing with the camera, and/or software can be used to capture and subsequently display the IR camera imagery on the computer. In one or more embodiments, a Red Hat Linux OS™ and software package can be used to interface, access, and capture the IR image from the thermal imaging system described in [123]. However, one or more embodiments of the invention are not limited to thermal (IR) imaging systems, and other imaging systems (e.g., UV) or data (cellular, molecular, and genomic) can be used for MBMS.

In one or more embodiments, the steps 200-210 can be implemented in multiple computers and/or using multiple imaging systems, each performing one or more of the steps 200-210 (e.g., using cloud computing). Results from each of the computers and image systems can be combined to improve identification of the abnormality.

System Functionality

A system according to one or more embodiments of the invention can provide the following functionalities.

First, the system can integrate several different image modalities, including visible light, Infrared (IR), Ultraviolet (UV), and Magnetic Resonance Imaging (MRI) scans (preoperative as well as intra-operative), and data sets including molecular and genomic/biopsy data (preoperative as well as intra-operative), if available, biopsy markers, and intra-operative ultrasound, in order to show a single 2D view of the surgical field combining the information from the multiple image sources. In one or more embodiments, this integration is achieved using a multimodality image registration module. Therefore, the 2D image will be transformed into a 3D image and 4D (mathematical predictive modeling) can be added to the $3^{rd}$ dimension.

Second, the system's view or display can include suggestive contours of the remaining tumor tissue, as computed by a tumor auto-delineation engine. An operator or observer (e.g., neurosurgeon) can see these contours in real time, as an overlay on the IR and visual images. The tissue indicated as a residual tumor by the auto-delineation method/system according to one or more embodiments can be inspected and biopsy markers can be extracted from those sites. The biopsy markers can be used for further validation of the delineation engine/resection margin, and later added to a reference database for further refinement of the auto-delineation method/system.

These two modules are discussed in further detail in the following sections.

A. Multimodality Image Registration

Images from different modalities, as well as biopsy markers (molecular/cellular genomic data), are typically in different coordinate systems. Thus, in one or more embodiments, they need to be co-registered with each other to align the images pixel-wise. To this end, the first step is camera calibration and data acquisition.

Camera Calibration According to One or More Embodiments

Calibration of the camera (i.e., IR or UV modality) is the process of finding the parameters of the camera, i.e., position, orientation, focal length, etc., that produced a given Multimodality Intraoperative Brain Mapping (e.g., IR image, UV image, and/or other images and/or cellular, molecular, genomic data). In this step, the experimental setup can be geometrically modeled by a 3×4 matrix which transforms two dimensional (2D) screen coordinates to three dimensional (3D) coordinates as well as a four dimensional (4D) mathematical predictive modeling system. This transformation corrects for effects of perspective projection and camera focal length in the Multimodality Intraoperative Brain Mapping (e.g., IR image, UV image, and/or other images or data), and thus helps with registration of MRI, UV and IR images of the tissue (e.g., patient brain). In addition, biopsy markers can be registered to the MRI and IR images. In this way, biopsy markers, if available, can be imported to improve the auto-delineation. Furthermore, the Multimodality Intraoperative Brain Mapping system's (e.g., IR image, UV image, and/or other imaging/data acquisition system)'s noise characteristics can be collected for better preprocessing of the MBMS images. The noise model developed for the camera being used also helps design a better tumor classifier. In one or more embodiments, Camera Calibration Toolbox for Matlab™ [40, 41] can be used to perform this step.

A similar calibration can be performed for the photographic camera and other imaging devices.

Image Alignment

While camera calibration aligns the images to a certain extent, in one or more embodiments, accurate pixel-wise alignment is needed to obtain good training and auto-classification results. This operation can be non-trivial since intensity values in each modality image can represent different contrast agents, namely temperature, hydrogen molecule density, and absorption spectrum, for example. In one or more embodiments, mutual information is used to provide alignment criteria for registration. Given two images $I_1$ and $I_2$, registration using mutual information comprises finding a displacement vector field u that deforms $I_2$ so that it aligns with $I_1$. The mutual information Du between images can be defined as:

$$D_u(I_1, I_2) = \int p_u(I_1, I_2) \log \frac{p_u(I_1, I_2)}{p(I_1)p_u(I_2)} dI_1 dI_2$$

where:

$I_1$ and $I_2$ represent intensity in each of the images, $p_u(I_1, I_2)$ is the joint probability distribution function of $I_1$ and $I_2$ that gives the probability that each of $I_1$ and $I_2$ falls in any particular range or discrete set of values specified for that variable, when $I_2$ is deformed by u, $p(I_1)$ is the marginal probability distribution of $I_1$ falling in any particular range specified for $I_1$, and $p(I_2)$ is the marginal probability distribution of $I_2$ falling in any particular range specified for $I_2$ when $I_2$ is deformed by u.

In one or more embodiments, the vector u that maximizes the mutual information (maximizing of mutual information registration or MMI registration [123]) is determined/computed. The $I_2$ is then expressed in co-ordinates displaced by u.

It has been shown that this information theoretic criterion is well suited for alignment of multimodality data [117, 118]. Such a registration has been implemented in Matlab™ using a 12 parameter affine model, and can be applied to perform the co-registration of IR, MRI, visual images, as well as and biopsy markers, to common coordinates.

Image-Processing System

One or more embodiments of the invention efficiently enhance and manipulate the captured camera imagery (e.g., IR or UV, or other multi-modal imagery) in near-real time (>5 femtoseconds or >5 picoseconds) using a suite of efficient image processing tools in Matlab™ (under Red Hat Linux OS™). For example, the suite can comprise [17, 18, 19]: (A) Contrast correction/enhancement; (B) Brightness correction/enhancement; (C) Red Green Blue (RGB) channel histogram equalization for luminance control under a wide range of lighting conditions; and (E) Edge detection.

B. Auto-Delineation Engine

In one or more embodiments, the auto-delineation engine employs a supervised learning method/system that operates as follows. The auto-delineation engine first learns incrementally, from human or AI expert-annotated Multimodality Intraoperative Brain Mapping (e.g., IR image, UV image, and/or other image and/or data), and visual image pairs, to distinguish tumor tissue (the training phase). Once trained, the auto-delineation engine is applied to perform auto-delineation in real time (the operating phase). In the training phase, the infrared image, MRI image, and visual image can be supplied along with the expert delineations as inputs. In the operating phase, IR, UV, MRI, and visual images can supplied as inputs to the classifier and the engine outputs the delineations.

Training Phase

In order to train the auto-delineation engine, one or more embodiments of the invention provide a "reference" database to store and annotate the Multimodality Intraoperative Brain Mapping (e.g., IR, UV, and/or other image or data) as well as the visual imagery of the tissue/tumor site. Neurosurgeons and/or medical care providers evaluate both the IR/UV and visual imagery and determine the delineation of the tumor resection margins. These delineations are graphically overlaid with the IR/UV and visual imagery and stored as a separate, "training" set of images (e.g., in the database). To further improve upon the initial delineations performed by the neurosurgeons/medical care providers, additional annotations, based, e.g., on biopsy samples, can be incorporated. The imagery delineated by the medical care providers is inputted as data to a learning method/system (e.g., based on Support Vector Machines, SVM). Once trained, the auto-delineation engine can be tested for accuracy in predicting the boundaries of brain tumors or other tumors, and re-validated each time additional training data is supplied. Although the process is described using IR/UV imagery, other multi-modal imagery (e.g., MRI, CT, etc.), can also be used to train the engine).

The method/system based on the Support Vector Machines (SVM) technique, according to one or more embodiments, is explained below.

One Class Support Vector Machines

One-class support vector machines construct a classifier only from a set of labeled positive training samples. The co registered IR data ($x_{ir}$), MRI data ($x_{mri}$), and visual data ($x_{op}$) are arranged in a feature vector $x=[x_{ir}, x_{op}, x_{mri}]$. The training dataset is indexed as $\chi=\{x|=1, 2, \ldots, 1\}$, where $x_i$ is the $i^{th}$ observation and 1 denotes the total number of labeled data points. A feature map is then computed, which maps the training data into a higher dimensional feature space F, using a mapping function $\Phi:\chi \to F$. Thus, the image of a training sample $x_i$ in $\chi$ is denoted by $\Phi(x_i)$ in F. Singular value decomposition (SVD) can be used to generate this mapping function. Since only the tumor is labeled, the objective function of one class SVM is denoted as $$\min_{W \in F, \eta \in F, b \in F} \left[ \frac{1}{2} W^T W + \frac{1}{\nu l} \sum_i \eta_i - b \right]$$

such that $W \cdot \Phi(x_i) \geq b - \eta_i$ where W represents the normal vector of the hyper-plane which represents the decision boundary, b represents the threshold function, $\eta$ is the slack variable, and the regularization term v is a user defined parameter which controls the trade-off and indicates the fraction of samples that should be accepted by the decision.

This objective function can be minimized (min) over W, $\eta$, and b using a quadratic programming (QP) optimization method. The inequality constraint can be imposed using Lagrange multiplier(s).

Figure 3:
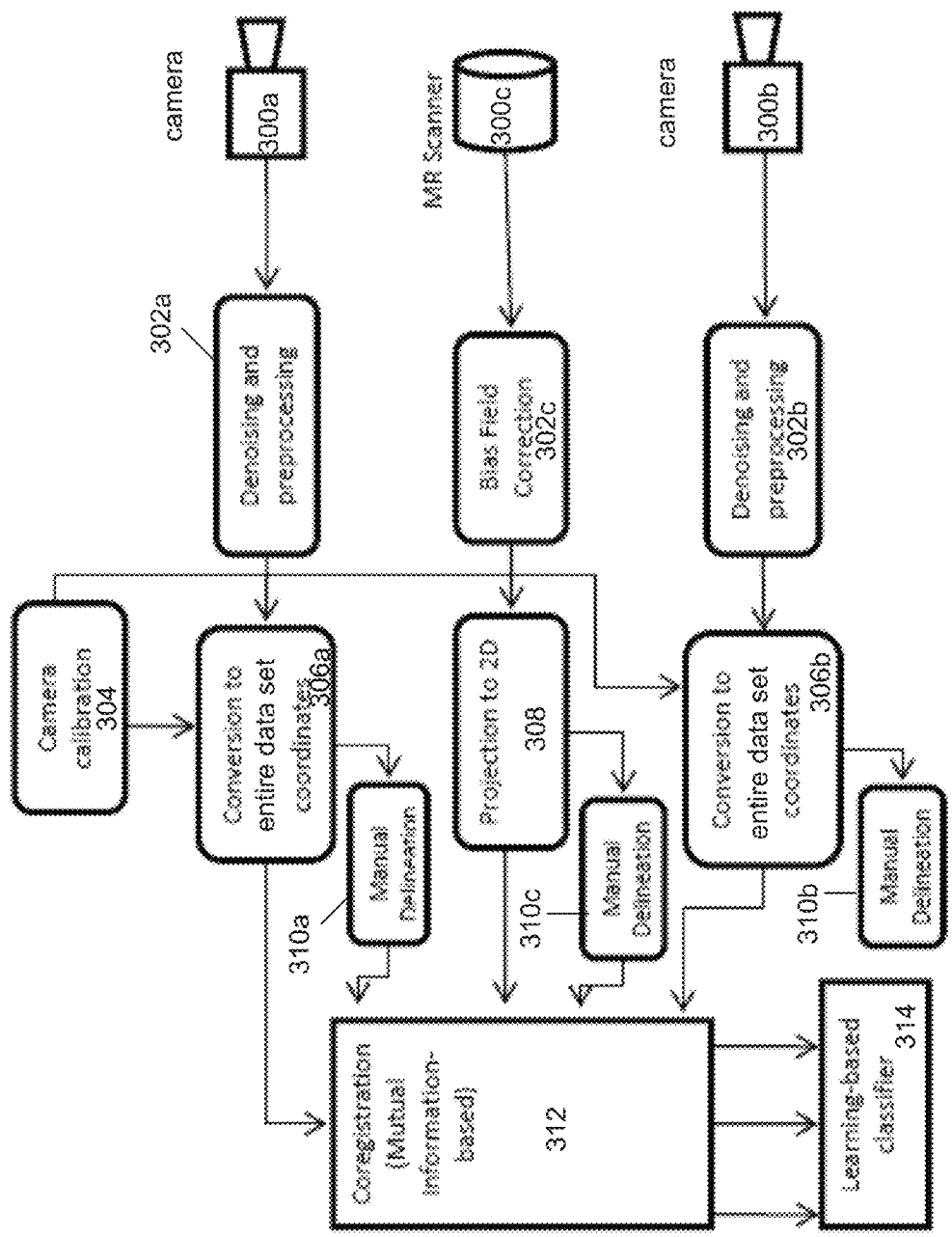
FIG. 3 is a block diagram illustrating an auto-delineation process in a training phase, according to one or more embodiments of the invention.

FIG. 3 is a block diagram illustrating the auto-delineation process in the training phase, according to one or more embodiments of the invention, comprising the following steps.

Blocks 300*a-c* represent capturing one or more images of tissue using a first camera 300*a* (e.g., UV camera or IR camera), a second camera (e.g., for visible light) 300*b*, and MRI scanner 300*c*. Cameras 300*a-b* are not limited to particular wavelengths, but typically image at different wavelengths to provide multi-modal imaging.

Blocks 302a-c represent pre-processing the images, comprising de-noising and pre-processing (blocks 302a and 302b) the one or more images taken with the camera 300a and the one or more images taken with the camera 300b, and bias field correction (block 302c) of the images taken with the MRI scanner 300c.

Block 304 represents calibration of the camera 300a and camera 300b. Blocks 306a and 306b represent conversion of the calibrated and pre-processed images obtained from the camera 300a and camera 300b, respectively, into an entire data set co-ordinate system. The conversion can enable matching/comparing/contrasting image points/pixels/elements obtained from each of the MBMS images/data with the entire data set (e.g., UV image, IR image, visible image, histology, cellular data) obtained using the MBMS system, so that the image element/point/pixel in the camera's 300a, 300b image correspondence to an abnormality can be identified (some MBMS data may indicate abnormalities and some may not). Thus, the image element/pixel from camera 300a, 300b can be replotted in the entire data set co-ordinate system so that comparison with other MBMS data can be made (and the any abnormality measured in the image can be identified).

Block 308 represents projecting the bias field corrected Multimodality Intraoperative Brain Mapping (e.g., MRI, CT, IR, UV, and/or other image or data) from a three dimensional (3D) representation into a 2D representation, as well as (optionally) a 4D mathematical image including predictive modeling.

Blocks 310a-b represent performing a manual delineation of the images in entire data set co-ordinates (i.e., from blocks 306a and 306b) to form manually delineated camera images, and Block 310c represents performing a manual delineation of the MRI images projected in 2D (i.e., from block 308) to form manually delineated MRI images.

Block 312 represents co-registering the manually delineated images represented in entire data set co-ordinates and the manually delineated MRI image projected in 2D, using a mutual information method (e.g., as part of image alignment as described above), to obtain a co-registered data/image.

Block 314 represents receiving the co-registered data/image, and analyzing the co-registered data/image in the learning based classifier using machine learning (e.g., SVM), so that the learning based classifier can learn to auto-delineate the abnormal tissue in one or more images.

Operating Phase

In one or more embodiments, the operating phase comprises the following steps.

1. Classifying Data from New Images

Abnormalities in the new images can be classified using the auto-delineation engine and machine learning trained during the training phase (e.g., using SVM).

2. Noise Reduction

The classification performed using SVM may contain artifacts (such as multiple disconnected components and outliers) since it does not take into account the spatial connectivity of the pixels, and thus may be relatively susceptible to noise. These artifacts can be removed by Markov Random Field (MRF) modeling [43] of the classifier and active contour segmentation for the final delineation. This can be performed by having additional "coherence" terms in the classifier that encourage similar pixel classification for neighboring pixels.

3. Active Contour Segmentation

Active contour is a framework for delineating a spatially-coherent object outline from a noisy 2D image. The segmented image generated in the operating phase can be noisy, especially at the boundary of the tumor. One or more embodiments of the invention use Insight Segmentation and Registration Toolkit (ITK™) for implementing active contours (e.g., in C++). In order to generate a smooth delineation of the tumor, active contour framework from the ITK™ toolkit can be employed. In one or more embodiments, gradient vector flow (GVF) snakes can be used for the model.

The GVK snake is an active contour model where the driving forces are spatial gradients of the image on which the snake model is applied. A GVK snake can be initialized based on the image (e.g., MRI) contour mapped to the classified IR image as described above. The GVF forces, namely the image gradient, are used to drive the snake, modeled as a physical object having a resistance to both stretching and bending, towards the boundaries of the object. The GVF forces can be calculated by applying generalized diffusion equations to both components of the gradient of an image edge map.

A variety of recent image segmentation methods [17, 18, 19, 20, 21] can also be used. Recent techniques for tumor localization include use Hidden-Markov model and mixture models. These techniques can be adapted and applied to the infrared images. Through feed-forward type neural nets [22, 23] and Hopfield attractor neural networks, [24] the image segments, delivered by the image segmentation methods above, can be classified as belonging to either tumor or normal tissue. The neural networks can be trained against the fully annotated and refined (through biopsies) "reference" database. For feed-forward type multi-layered perceptron systems, a well-established Error-Back-Propagation method [25, 26] can be used. The Projection Rule or Pseudoinverse [22, 23, 24, 27], which is a method for storing highly correlated patterns, can be employed for Hopfield attractor neural networks. The advantage of attractor networks over feed-forward type networks lies in the successful discrimination between stored stimulation patterns even in the presence of noise.

In one or more embodiments, the operation phase needs to be performed in real time during the surgery and therefore the speed of delineation method is important. Efficient methods/systems from the ITK toolkit can be used to perform this task in real time.

In one or more embodiments, the SVM method/system can be implemented in Matlab™ (as an example of existing system) using tools available from the Classification Toolbox. However, one or more embodiments of the invention are not limited to the use of a Matlab™ system.

The training phase of the delineation software can be conducted offline using the reference database. The operating phase of performing actual delineations can take place in real time on a computer connected to the operating room. Once a surgery is over, manual delineations can be performed on the Multimodality Intraoperative Brain Mapping (e.g., IR, UV, MRI, CT, and/or other image or data) of the patient after the surgery. In addition, the cellular and molecular indications could be identified and integrated in the system, during the surgery.

Figure 4:
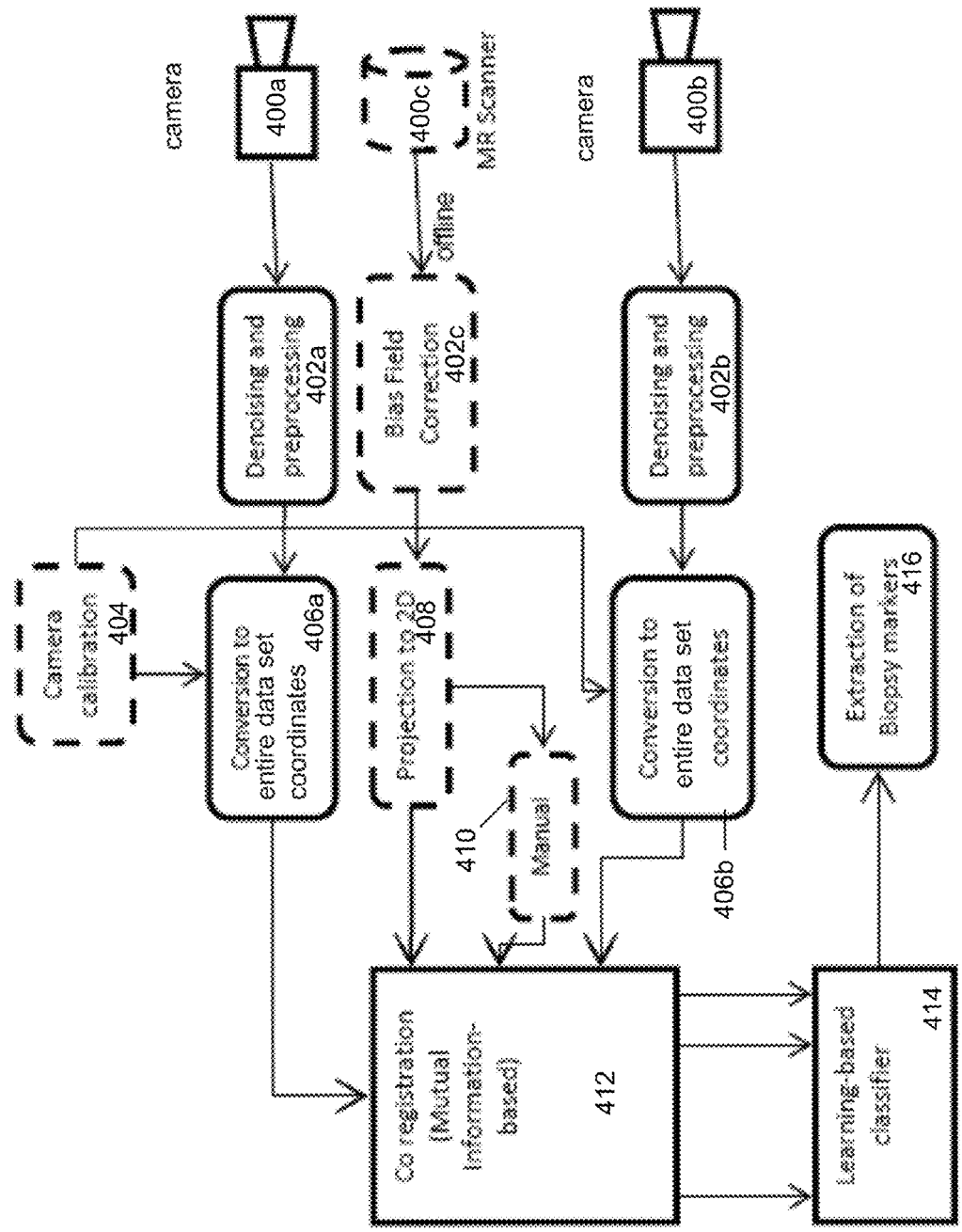
FIG. 4 is a block diagram illustrating an auto-delineation process in an operating phase, according to one or more embodiments of the invention.

FIG. 4 is a block diagram illustrating the auto-delineation process in the operation phase, according to one or more embodiments of the invention, comprising the following steps.

Blocks 400a-c represent capturing one or more images of tissue using a first camera (e.g., UV or IR camera) 400a, a second camera (e.g., for visible light) 400b, and MRI scanner 400c. Cameras 400a-b are not limited to particular wavelengths, but typically image at different wavelengths to provide multi-modal imaging.

Blocks 402a-c represent pre-processing the images, comprising de-noising and pre-processing (402a and 402b) the one or more images taken with the camera 400a and the one or more images taken with the camera 400b, and bias field correction 402c of the images taken with the MRI scanner 400c.

Block 404 represents calibration of the camera 400a and camera 400b. Blocks 406a and 406b represent conversion of the calibrated and pre-processed images obtained from the camera 400a and camera 400b, respectively, into an entire data set co-ordinate system. The conversion can enable matching/comparing/contrasting image points/pixels/elements obtained from each of the MBMS images/data with the entire data set (e.g., UV image, IR image, visible image, histology, cellular data) obtained using the MBMS system, so that the image element/point/pixel in the camera's 400a, 400b image correspondence to an abnormality can be identified (some MBMS data may indicate abnormalities and some may not). Thus, the image element/pixel from camera 400a, 400b can be replotted in the entire data set co-ordinate system so that comparison with other MBMS data can be made (and the any abnormality measured in the image can be identified).

Block 408 represents projecting the bias field corrected MRI image from a 3D into a 2D representation.

Block 410 represents performing a manual delineation of the MRI images projected in 2D (i.e. from Block 408) to form a manually delineated MRI image.

Block 412 represents co-registering the images represented in entire data set co-ordinates and the manually delineated MRI image projected in 2D, using a mutual information method (e.g., as part of image alignment as described above), to obtain co-registered data.

Block 414 represents receiving the co-registered data in the learning based classifier, wherein the learning based classifier uses the training data obtained in the training phase (e.g., FIG. 3) to auto-delineate abnormal regions in the co-registered data.

Block 416 represents extracting one or more molecular and cellular indicators using the information learned from the learning based classifier.

Validation of the Overall Approach (Biopsy-Molecular and Cellular Indicators/Expert Delineations)

In order to perform validation of the overall system, one or more embodiments of the invention can use data obtained from randomized trials obtained from multiple medical centers. In one or more embodiments, biopsy marker extraction can be used for validation. The biopsy marker extraction in control data can be performed without using the auto-delineation microscope, while surgery on the test subjects can be performed using a microscope system which shows tumor hotspots as delineations. The accuracy of biopsy marker extraction can be compared by T-test.

Validation of Auto-Delineation Method/System

The performance of the delineation system, namely, delineation accuracy can be evaluated using validation techniques, including, but not limited to, pattern classification [43], Cross Validation [44], and Leave one-out validation. In addition, false alarm (false positive) and miss (true negative) rates can be compared and receiver operating characteristic (ROC) curves for different estimators can also be compared. The parameters of the delineation method/system can be tuned by using the performance estimates from these techniques.

Additional Considerations

In one or more embodiments, blood artifacts, tissues, and blood vessels might interfere with the temperature profile observed from the intraoperative imaging system of the abnormal tissue. One or more embodiments estimate that this should not be a significant problem because similar artifacts are present in the training set as well, and as such, the learning based classifier is trained to ignore them. However, in embodiments where these artifacts are a significant problem, a semi-automated mode based protocol for extraction of biopsy markers can be used in which the neurosurgeon/medical care provider chooses locations of biopsy markers at his/her discretion. If the classification fails due to these artifacts, the software can alert the neurosurgeon/medical care provider. In that case, the neurosurgeon/medical care provider can switch to a default procedure for biopsy marker extraction.

In one or more embodiments, the temperature profile at different stages of the tumor might be different and therefore might not be sharp at the edges. If this is an obstacle in training the classifier, fuzzy classification of the tumor tissue can be performed, assigning probabilities to each pixel in the MBMS screen/image/data (comprising, e.g., IR, UV, and/or other images) about the tissue boundary. These probabilities can be overlaid on the microscope screen and a protocol for extracting biopsy markers from highly probable sites can be implemented.

Hardware Environment

Figure 5:
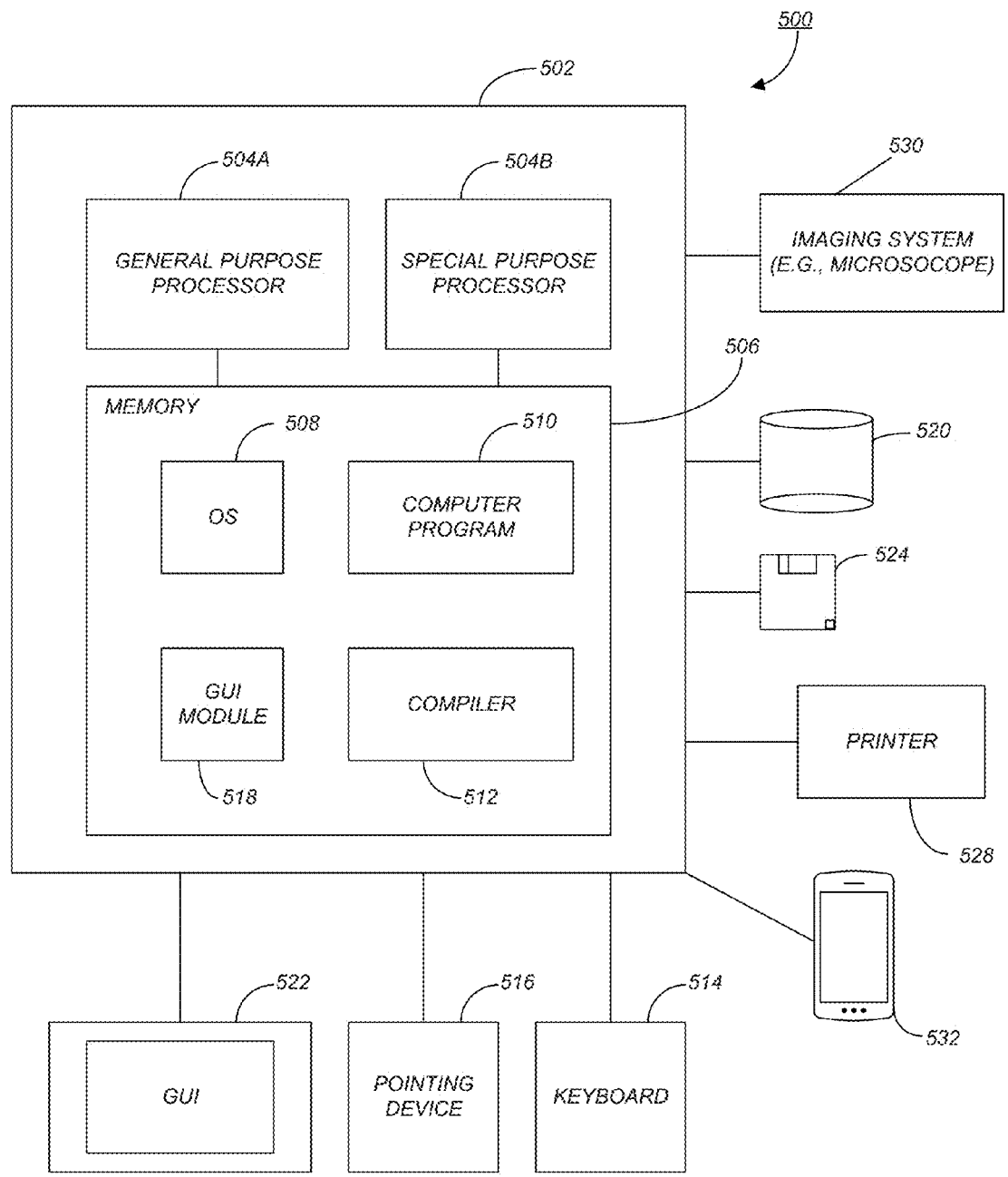
FIG. 5 is an exemplary hardware and software environment used to implement one or more embodiments of the invention.

FIG. 5 is an exemplary hardware and software environment 500 used to implement one or more embodiments of the invention. The hardware and software environment includes a computer 502 and may include peripherals. Computer 502 may be a user/client computer, server computer, or may be a database computer. The computer 502 comprises a general purpose hardware processor 504A and/or a special purpose hardware processor 504B (hereinafter alternatively collectively referred to as processor 504) and a memory 506, such as random access memory (RAM). The computer 502 may be coupled to, and/or integrated with, other devices, including input/output (I/O) devices such as a keyboard 514, a cursor control device 516 (e.g., a mouse, a pointing device, pen and tablet, touch screen, multi-touch device, etc.) and a printer 528. In one or more embodiments, computer 502 may be coupled to, or may comprise, a portable or media viewing/listening device 532 (e.g., an MP3 player, iPod™, Nook™, portable digital video player, cellular device, personal digital assistant, etc.). In yet another embodiment, the computer 502 may comprise a multi-touch device, mobile phone, gaming system, internet enabled television, television set top box, or other internet enabled device executing on various platforms and operating systems.

In one embodiment, the computer 502 operates by the general purpose processor 504A performing instructions defined by the computer program 510 under control of an operating system 508. The computer program 510 and/or the operating system 508 may be stored in the memory 506 and may interface with the user and/or other devices to accept input and commands and, based on such input and commands and the instructions defined by the computer program 510 and operating system 508, to provide output and results.

Output/results may be presented on the display 522 or provided to another device for presentation or further processing or action. In one embodiment, the display 522 comprises a liquid crystal display (LCD) having a plurality of separately addressable liquid crystals. Alternatively, the display 522 may comprise a light emitting diode (LED) display having clusters of red, green and blue diodes driven together to form full-color pixels. Each liquid crystal or pixel of the display 522 changes to an opaque or translucent state to form a part of the image on the display in response to the data or information generated by the processor 504 from the application of the instructions of the computer program 510 and/or operating system 508 to the input and commands. The image may be provided through a graphical user interface (GUI) module 518. Although the GUI module 518 is depicted as a separate module, the instructions performing the GUI functions can be resident or distributed in the operating system 508, the computer program 510, or implemented with special purpose memory and processors.

In one or more embodiments, the display 522 is integrated with/into the computer 502 and comprises a multi-touch device having a touch sensing surface (e.g., track pod or touch screen) with the ability to recognize the presence of two or more points of contact with the surface. Examples of multi-touch devices include mobile devices (e.g., iPhone™ Nexus S™, Droid™ devices, etc.), tablet computers (e.g., iPad™, HP Touchpad™), portable/handheld game/music/video player/console devices (e.g., iPod Touch™, MP3 players, Nintendo 3DS™, PlayStation Portable™, etc.), touch tables, and walls (e.g., where an image is projected through acrylic and/or glass, and the image is then backlit with LEDs).

Some or all of the operations performed by the computer 502 according to the computer program 510 instructions may be implemented in a special purpose processor 504B. In this embodiment, the some or all of the computer program 510 instructions may be implemented via firmware instructions stored in a read only memory (ROM), a programmable read only memory (PROM) or flash memory within the special purpose processor 504B or in memory 506. The special purpose processor 504B may also be hardwired through circuit design to perform some or all of the operations to implement the present invention. Further, the special purpose processor 504B may be a hybrid processor, which includes dedicated circuitry for performing a subset of functions, and other circuits for performing more general functions such as responding to computer program 510 instructions. In one embodiment, the special purpose processor 504B is an application specific integrated circuit (ASIC).

The computer 502 may also implement a compiler 512 that allows an application or computer program 510 written in a programming language such as C, C++, Assembly, SQL, Python, Prolog, MATLAB™, Ruby, Rails, Haskell, or other language to be translated into processor 504 readable code. Alternatively, the compiler 512 may be an interpreter that executes instructions/source code directly, translates source code into an intermediate representation that is executed, or that executes stored precompiled code. Such source code may be written in a variety of programming languages such as Java™, JavaScript™, Perl™, Basic™, etc. After completion, the application or computer program 510 accesses and manipulates data accepted from I/O devices and stored in the memory 506 of the computer 502 using the relationships and logic that were generated using the compiler 512.

The computer 502 can also be comprised in, or connected to, a Multimodality Brain Mapping System (MBMS) providing IR, UV, and/or other imaging or data (for example), either microscopically (using a microscope) and/or endoscopically (using an endoscope). For example, the computer 502 can be comprised in, or connected to, a scope. In one or more embodiments, one or more of the processors 504 implement the learning method/system or methods of imaging or identifying abnormal tissue according to one or more embodiments of the invention.

The computer 502 also optionally comprises an external communication device such as a modem, satellite link, Ethernet card, or other device for accepting input from, and providing output to, other computers 502.

In one embodiment, instructions implementing the operating system 508, the computer program 510, and the compiler 512 are tangibly embodied in a non-transitory computer-readable medium, e.g., data storage device 520, which could include one or more fixed or removable data storage devices, such as a zip drive, floppy disc drive 524, hard drive, CD-ROM drive, tape drive, etc. Further, the operating system 508 and the computer program 510 are comprised of computer program 510 instructions which, when accessed, read and executed by the computer 502, cause the computer 502 to perform the steps necessary to implement and/or use the present invention or to load the program of instructions into a memory 506, thus creating a special purpose data structure causing the computer 502 to operate as a specially programmed computer executing the method steps described herein. Computer program 510 and/or operating instructions may also be tangibly embodied in memory 506 and/or data communications devices, thereby making a computer program product or article of manufacture according to the invention. As such, the terms "article of manufacture," "program storage device," and "computer program product," as used herein, are intended to encompass a computer program accessible from any computer readable device or media. In one or more embodiments, computer 502 may be coupled to, or may comprise, or be integrated in, an imaging system 530 (e.g., optics, microscope, microscope optics, camera). For example, the processing (e.g., the machine learning) can be performed in the imaging system 530.

Of course, those skilled in the art will recognize that any combination of the above components, or any number of different components, peripherals, and other devices, may be used with the computer 502.

Figure 6:
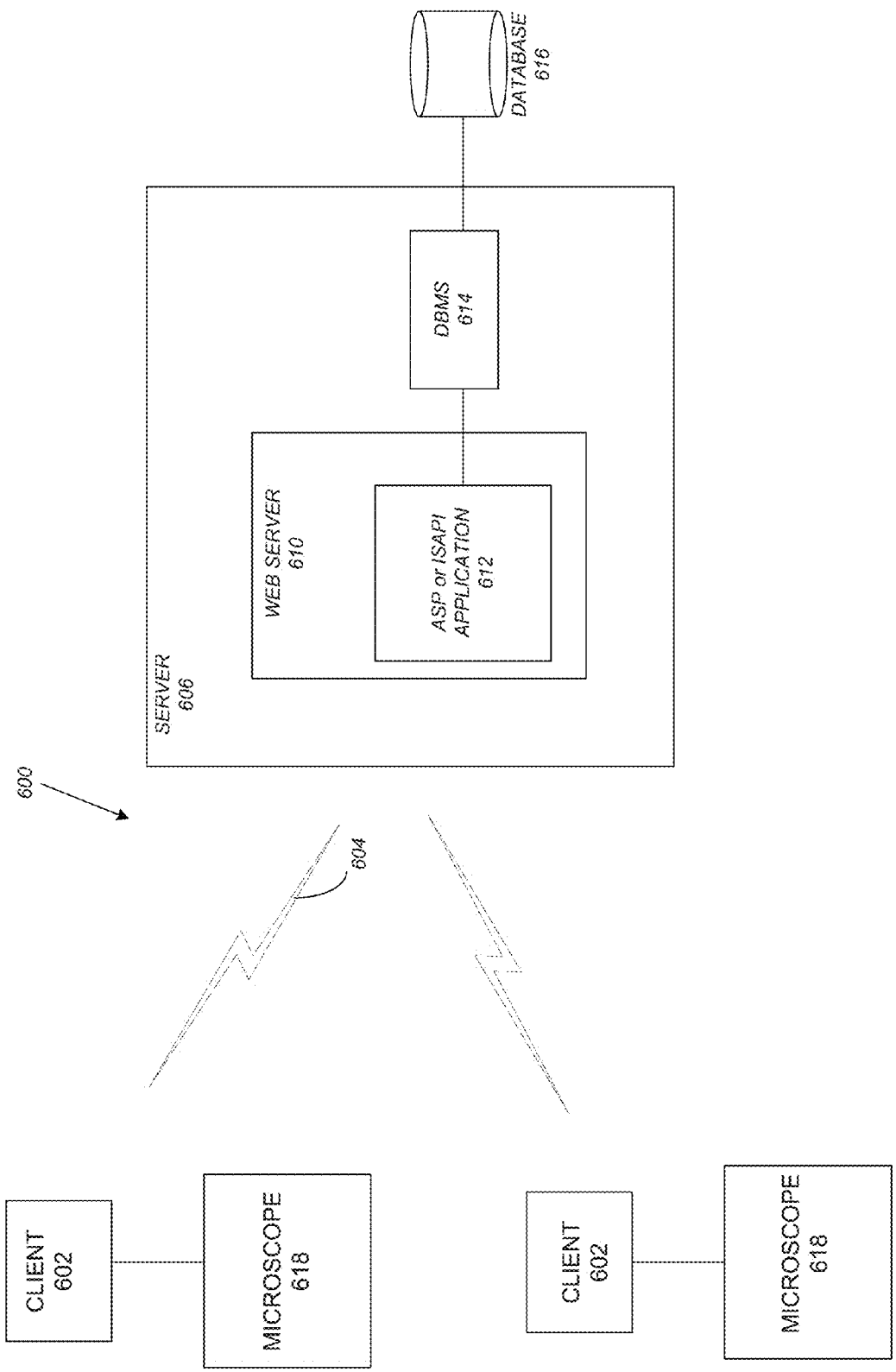
FIG. 6 schematically illustrates a typical distributed computer system, according to one or more embodiments of the invention.

FIG. 6 schematically illustrates a typical distributed computer system 600 using a network 604 to connect client computers 602 to server computers 606. A typical combination of resources may include a network 604 comprising the Internet, LANs (local area networks), WANs (wide area networks), SNA (systems network architecture) networks, or the like, clients 602 that are personal computers or workstations (as set forth in FIG. 5), and servers 606 that are personal computers, workstations, minicomputers, or mainframes (as set forth in FIG. 5). However, it may be noted that different networks such as a cellular network (e.g., GSM [global system for mobile communications] or otherwise), a satellite based network, or any other type of network may be used to connect clients 602 and servers 606 in accordance with embodiments of the invention.

A network 604 such as the Internet connects clients 602 to server computers 606. Network 604 may utilize ethernet, coaxial cable, wireless communications, radio frequency (RF), etc. to connect and provide the communication between clients 602 and servers 606. Clients 602 may execute a client application or web browser and communicate with server computers 606 executing web servers 610. Such a web browser is typically a program such as MICROSOFT INTERNET EXPLORER™, MOZILLA FIREFOX™, OPERA™, APPLE SAFARI™, GOOGLE CHROME™, etc. Further, the software executing on clients 602 may be downloaded from server computer 606 to client computers 602 and installed as a plug-in or ACTIVEX™ control of a web browser. Accordingly, clients 602 may utilize ACTIVEX™ components/component object model (COM) or distributed COM (DCOM) components to provide a user interface on a display of client 602. The web server 610 is typically a program such as MICROSOFT'S INTERNET INFORMATION SERVER™

Web server 610 may host an Active Server Page (ASP) or Internet Server Application Programming Interface (ISAPI) application 612, which may be executing scripts. The scripts invoke objects that execute business logic (referred to as business objects). The business objects then manipulate data in database 616 through a database management system (DBMS) 614. Alternatively, database 616 may be part of, or connected directly to, client 602 instead of communicating/obtaining the information from database 616 across network 604. When a developer encapsulates the business functionality into objects, the system may be referred to as a component object model (COM) system. Accordingly, the scripts executing on web server 610 (and/or application 612) invoke COM objects that implement the business logic. Further, server 606 may utilize MICROSOFT'S™ Transaction Server (MTS) to access required data stored in database 616 via an interface such as ADO (Active Data Objects), OLE DB (Object Linking and Embedding DataBase), or ODBC (Open DataBase Connectivity).

Generally, these components 600-616 all comprise logic and/or data that is embodied in/or retrievable from device, medium, signal, or carrier, e.g., a data storage device, a data communications device, a remote computer or device coupled to the computer via a network or via another data communications device, etc. Moreover, this logic and/or data, when read, executed, and/or interpreted, results in the steps necessary to implement and/or use the present invention being performed.

Although the terms "user computer", "client computer", and/or "server computer" are referred to herein, it is understood that such computers 602 and 606 may be interchangeable and may further include thin client devices with limited or full processing capabilities, portable devices such as cell phones, notebook computers, pocket computers, multi-touch devices, and/or any other devices with suitable processing, communication, and input/output capability.

Embodiments of the invention are implemented as a software application on a client 602 or server computer 606. Further, as described above, the client 602 or server computer 606 may comprise a thin client device or a portable device that has a multi-touch-based display.

Of course, those skilled in the art will recognize that any combination of the above components, or any number of different components, peripherals, and other devices, may be used with computers 602 and 606.

Possible Modifications and Variations

One or more embodiments of the invention further comprise growing the database of training data over time and/or linking a plurality of microscopes together through cloud computing. This data network can create metadata that can be used to achieve significantly more precise behavioral pattern recognition of brain malignancies based on hundreds of thousands of cases operated on by different surgeons with different levels of expertise across the globe.

FIG. 6 further illustrates a cloud and/or parallel computing system, according to one or more embodiments, wherein the data obtained from the images captured in a plurality of microscopes 618 is shared over the network 604, so that the machine learning learns to identify one or more abnormalities from the data obtained from a plurality of microscopes 618 obtaining images during surgical (or other) procedures on a plurality of different patients/cases. Thus, the machine learning can learn from the data obtained from different surgeries. The machine learning can be implemented on a plurality of computers in the system, e.g., working in parallel and/or each performing different processes.

Logical Flow for Identifying Abnormal Cells

Figure 7:
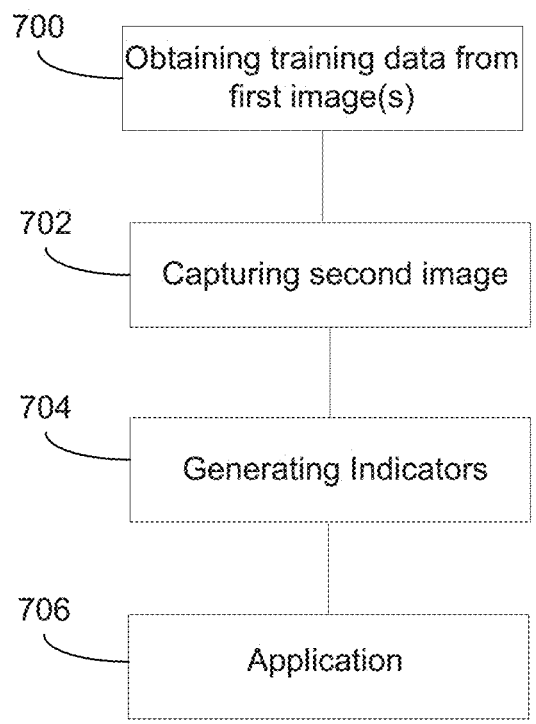
FIG. 7 is a flowchart illustrating a method of identifying abnormal cells, according to one or more embodiments of the invention.

FIG. 7 is a flowchart illustrating a method of identifying abnormal cells in a patient/tissue, according to one or more embodiments of the invention.

Block 700 represents obtaining training data from first data or one or more first images of tissue, wherein one or more abnormal regions and one or more normal regions (of a patient's tissue or of one or more tissues) are identified. The training data can comprise human or AI delineations/classification of the abnormal regions in the one or more first images.

Block 702 represents receiving/capturing one or more second images of the tissue, the second images captured at a later time than the one or more first images/first data, and/or using a different imaging technique/system 630 than was used to capture the one or more first images, and/or using a Multimodality Brain Mapping System (MBMS) comprising IR, UV, and/or other imaging system or data acquisition system.

Block 704 represents generating, using machine learning, one or more viewable indicators identifying one or more abnormal cells and/or normal cells in the one or more second images. The training data can be inputted to, and the machine learning method/system can be implemented on, a machine such as computer 502/606 (e.g., in a machine learning unit/processor of the computer). The machine learning method/system can be trained using the training data to identify one or more biological cells in the second image as abnormal or normal (e.g., trained to distinguish one or more abnormal cells from one or more normal cells of the tissue shown in the second image).

The machine learning can use pattern recognition or recognize regularities or correlations in data obtained from the first and second images. While the pattern recognition system can be trained from labeled "training" data (supervised learning), other methods/systems can also be used to discover previously unknown patterns (unsupervised learning), or a combination of supervised and unsupervised learning can be used (semi-supervised learning). The learning method/system can use a pattern recognition method/system to predict a pattern of growth of, and/or location of, the one or more abnormal cells in the second image.

The one or more viewable indicators can be generated in real time or dynamically (e.g., in less than 5 picoseconds) as the image is formed/captured.

Block 706 represents using the learning method/system in an application, for example with a microscope. The learning method/system can be implemented on one or more processors or computers integrated with the microscope or connected to the microscope, e.g., wirelessly or via a wired network connection (e.g., in a cloud computing based system). Thus, the indicators can be viewable on the one or more second images formed in a (e.g., digital) microscope/endoscope, (e.g., digital) camera, (e.g., digital) endoscope, or other imaging system/MBMS. The second image can be an image captured during a surgical procedure on the tissue in a patient, and the one or more first images can be images (e.g., MRI, CT, Positron Emission Tomography (PET)) as part of the MBMS-system captured prior to the surgical procedure. For example, metadata obtained from the one or more first images can be brought together to enable analysis of the image formed in a microscope/endoscope in real time and allow the artificial intelligence (e.g., provided by the learning method/system) of the microscope reach out to all aspects of the data in pre-op, intra-, and post-op (past surgeries), and in the intra-operative data set. This can help surgeons not only differentiate between normal and abnormal tissue but also help the device teach itself so the microscope/endoscope becomes a member of surgical team rather than a device. The technology can inform surgeons where to look at for diseased tissue, which has never been done and is revolutionary. The technology can also inform medical care providers what adjunctive therapy should be applied and where, what would be the predictive outcome of the surgery based on the past numbers of cases, and what should be anticipated in the future. Current solutions include use of intra operative CT, MRI, and optical (visible, ultra-violet, near infrared, infrared, etc.) as a single modality. In this regard, integration of multimodality imaging system/MBMS with artificial intelligence and software that helps pattern recognition has not been attempted.

The learning method/system can comprise a support vector machine (SVM). For example, the SVM can analyze the training data and recognize patterns or correlations in the training data, wherein the training data is classified and subjected to a regression analysis. For example, given a set of training examples, each labeled as being normal or abnormal (e.g., cancerous or non-cancerous), a support vector training method/system can build a model that assigns new examples as being abnormal or normal (e.g., a non-probabilistic binary linear classifier). The SVM can perform a non-linear classification using a kernel method, mapping the inputs (training data or new data) into high-dimensional feature spaces.

Figure 8:
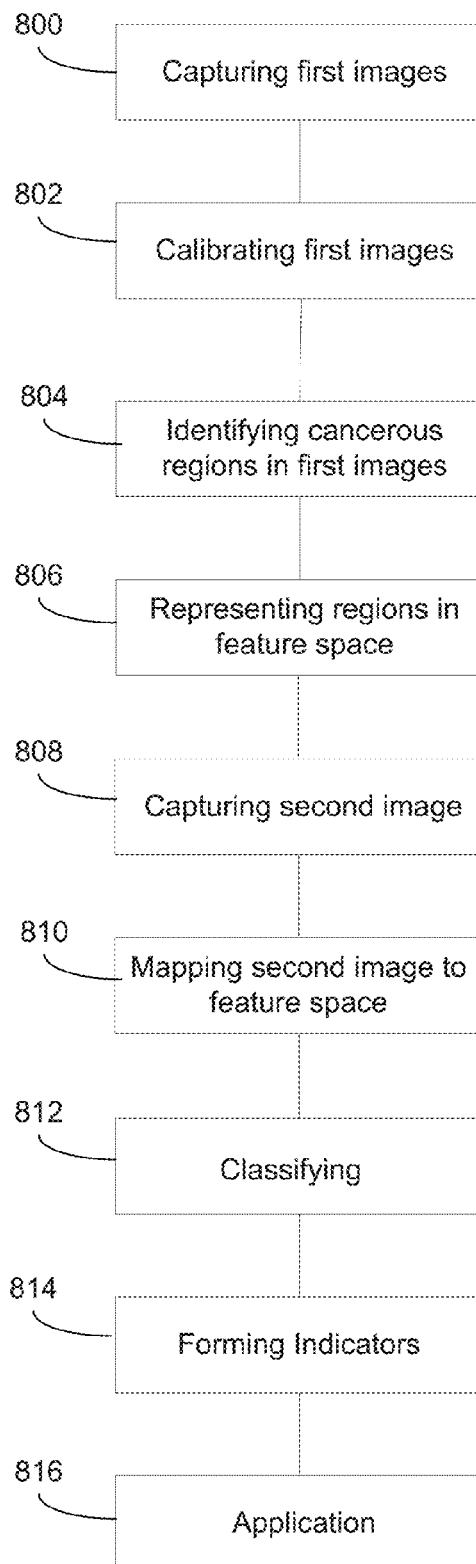
FIG. 8 is a flowchart illustrating a method of classifying abnormal cells, according to one or more embodiments of the invention.

FIG. 8 is a flowchart illustrating a method for identifying one or more abnormal cells in an image of a patient's tissue (e.g., that could be implemented by a SVM). The method can comprise the following steps.

Block 800 represents receiving and/or capturing one or more first images of one or more first tissues (e.g., a thermal or UV image) of one or more first patients. The first patients can comprise different patients, for example.

Block 802 represents calibrating the one or more first images, if necessary. The step can comprise converting the first images to a same entire data set co-ordinate system and/or co-registering the first images. For example, the step can comprise registering multimodal images/first data obtained from two or more of the following: biopsy, Infrared Imaging, Diffusion Tensor Imaging (DTI), Computed Tomography (CT), Magnetic Resonance Imaging (MRI), Brain Mapping Ultrasound, cellular, molecular and genomic data, and Functional MRI (FMRI) to form a registered image and/or patient data. In one or more embodiments, the registering can achieve geometrical correspondence between the images, or geometric alignment/overlaying of the images to compare corresponding regions in each image volume/area, e.g., such that from the coordinates of a point in one image, the coordinates of the geometrically corresponding point in each of the other images can be obtained. For example, the registering can be such that anatomically identical points can be located and compared in each of the images. The registering can be such that the features measured in each of the images are visible in one image.

Block 804 represents identifying one or more abnormal regions and one or more normal regions of the one or more first tissues shown in the first images (e.g., using expert delineation provided by a medical care provider). The one or more abnormal regions can be identified in at least two co-registered first images and/or patient data (e.g., showing different properties of the tissue). The identification can be improved using state-of-the-art computer simulations (e.g., [121]) and/or predictive oncology (e.g., [122]) which is advancing field. The expert delineation can be inputted into a database on a computer or inputted/marked by a user (medical image) on an image in a computer. A training database can be provided wherein one or more image elements in the one or more first images or registered image are identified by a medical care provider as abnormal or normal.

Block 806 represents representing the identified abnormal/normal (e.g., cancerous/non-cancerous) regions with feature vectors in a feature space (e.g., as defined and performed by a support vector machine). A feature can be any distinctive aspect, quality, or characteristic of abnormal/normal regions, and a feature vector can be an n-dimensional vector of numerical or symbolic (e.g., color) features that represent the abnormal or normal regions. For example, the feature vector comprising the combination of d features can be represented as a d-dimensional column vector. When representing images, the feature values might correspond to the pixels or voxels of an image. The feature space can be the vector space associated with/defined by these feature vectors.

The step 806 can comprise representing the abnormal regions of the first images/registered image with first feature vectors defining first coordinates/points/regions in a feature space, and representing the normal regions of the first image with second feature vectors defining second coordinates/points/regions in the feature space (e.g., the abnormal and normal regions can be represented as points in the feature space, as in a scatter plot or graph). The feature space can be selected such that at least some of the first coordinates/points and at least some of the second coordinates/points are on opposite sides of a hyper-plane in the feature space. For example, at least some of the first coordinates can be on a first side of the hyper-plane and at least some of the second coordinates can be on a second side of the hyper-plane. The step can comprise finding the appropriate feature space and optimizing the co-ordinates of the hyper-plane in the feature space (e.g., using regression analysis). The step can further comprise optimizing the hyper-plane using error correction methods/systems using the validation techniques discussed above.

Block 808 represents receiving (and optionally capturing) one or more second images of one or more second tissues of a second patient (the second patient can be the same as one or more of the first patients, or can be a different patient from one or more of the first patients). The one or more second tissues can be the same as one or more of the first tissues, or different from the first tissues. The second image can comprise an image of the same or a different region of the tissue imaged with the one or more first images. The second images (e.g., comprising an optical image) can be captured in an imaging system (e.g., a camera, e.g., during a surgical procedure) and/or using a MBMS. The first image and second images can show different properties/characteristics of the tissue. The step can comprise co-registering/calibrating the images if necessary.

Block 810 represents mapping one or more image regions/elements, comprising one or more regions/pixels/voxels of the one or more second images, to one or more image coordinates/points/regions in the feature space, so that the one or more image regions are represented as feature vectors (image feature vectors) in the feature space.

Figure 9:
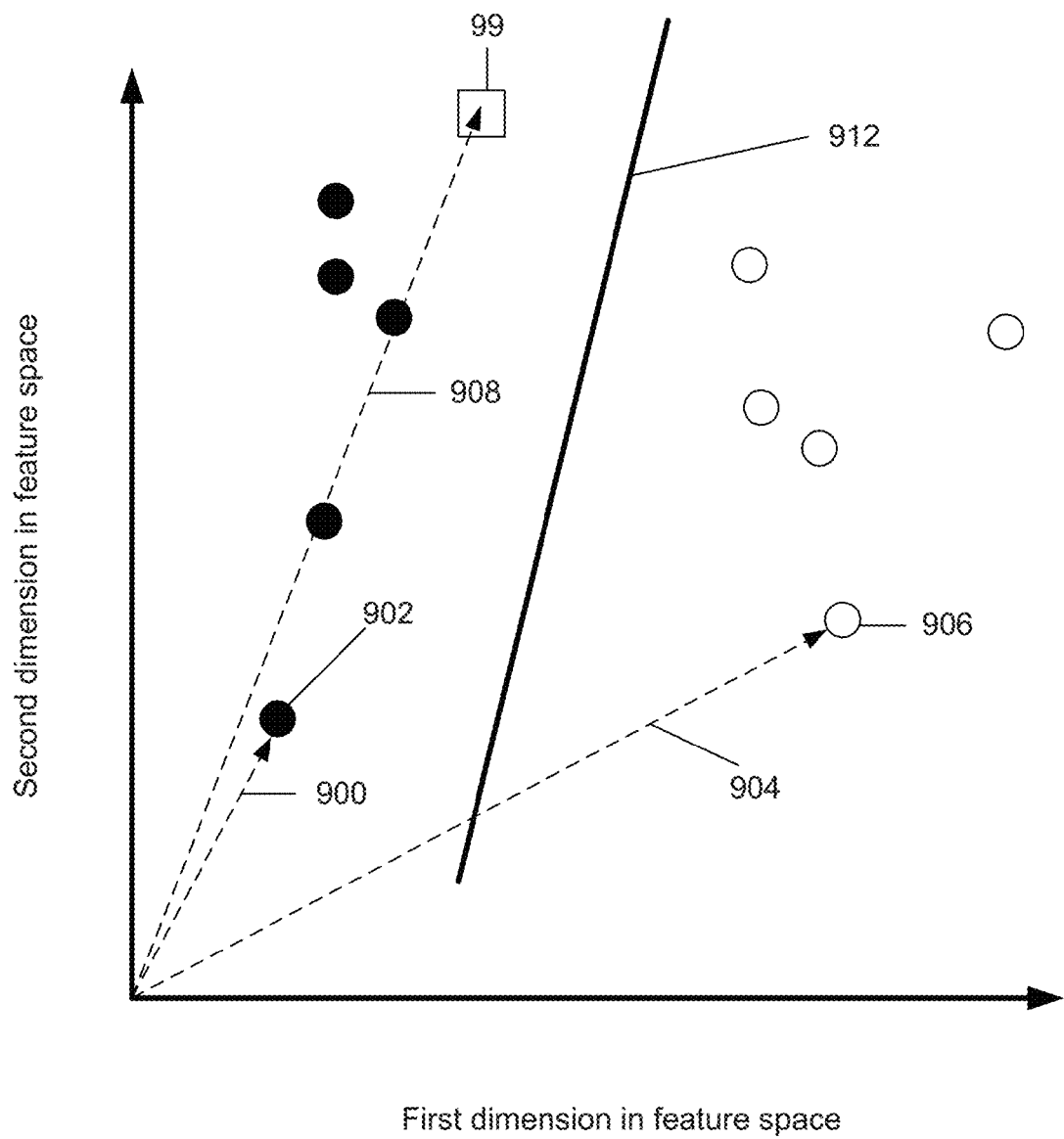
FIG. 9 is a schematic of a feature space according to one or more embodiments of the invention.

Block 812 represents classifying the image feature vectors or image coordinates in the feature space (e.g., using SVM). The step can comprise classifying one or more of the image coordinates as one or more abnormal coordinates or normal coordinates depending on one or more factors, including which side of the hyper-plane the one or more image co-ordinates lie, and/or proximity of the one or more image coordinates to the first abnormal coordinates and/or the hyper-plane. For example, the image region can be classified as an abnormal image region if the image region is mapped to one or more of the abnormal coordinates according to the mapping (i.e., closer to the first coordinates and/or on the first side of the hyper-plane); such image region can be classified as a normal image region if the image region is mapped to one or more of the normal coordinates according to the mapping (i.e., closer to the second coordinates and/or on the second side of the hyper-plane). FIG. 9 illustrates an example of a feature space having a first dimension and a second dimension, illustrating the first feature vector 900 defining first coordinate 902, the second feature vector 904 defining second coordinate 906, image feature vector 908 defining abnormal coordinate 910, and hyper-plane 912.

Block 814 represents forming the one or more indicators to indicate the one or more cells as abnormal if the one or more cells are in the abnormal image region, and/or forming the one or more indicators to indicate the one or more cells as normal if the one or more cells are in the normal image region. The forming can comprise overlaying, integrating, or compositing the second image with the indicators in the display of the imaging system. The indicators can be provided in a visually distinguishable manner, for example using colors, intensity, contrast, highlighting, flashing, or sound, etc.

Block 816 represents using the indicators in an application, for example during a surgical procedure. For example, the second image can comprises an optical image captured during a surgical procedure on a patient, and the one or more viewable indicators can enable the abnormal region to be surgically removed from the patient, during the surgical procedure, with increased precision by reducing damage to normal tissue.

Steps 700-706 and 800-816 can be implemented in one or more processors (as described herein) interfaced/coupled to an imaging system 530, such as a microscope/endoscope. In one or more embodiments, software implementing the method(s) of steps 800-816 can be converted to a C++ standalone library and run as a standalone binary on a variety of platforms including Redhat Linux™, Mac OS X™ and Windows Vista™, for example.

Furthermore, steps 800-816 or 800-806 can be implemented using a plurality of microscopes/surgical microscopes/imaging systems. In one or more embodiments, the microscopes 718 can be connected to learn, share, and access data from one another, e.g., over a network 704 (as illustrated in FIG. 6) using cloud computing or parallel computing. Multi-central parallel computing and machine learning can be provided. Thus, FIGS. 5-8 illustrate the method can comprise obtaining the one or more first images of one or more patients captured with one or more first microscopes 618; obtaining the second image of a second patient captured with a second microscope 618, wherein the second patient is different from the one or more patients; connecting the first and second microscopes using a cloud and/or parallel computing system 602, 606, that provides the machine learning; and wherein the training data obtained from the one or more first images captured in the first microscopes 618 is shared so that the machine learning learns from the training data to identify the abnormality in the second image.

As used throughout this disclosure, an abnormality, one or more abnormalities, one or more abnormal cells, and one or more abnormal regions can comprise, but are not limited to, cancer, one or more cancerous regions or one or more cancerous cells, one or more tumors, one or more epileptic regions or one or more epileptic cells, and/or one or more arteriovenous malformations in a patient/one or more tissues of a patient. The patient can comprise an animal or human patient and the tissue/cells can comprise animal, human, or plant tissue/cells. Thus, one or more embodiments of the invention can be extended to identifying disease generally, e.g., identifying diseased regions/tissue/cells from non-diseased regions/tissue/cells that do not have the disease. One or more embodiments of the invention can identify regions/cells that are not regular, do not conform to a standard type, that are not natural, that are not normal, or that are not healthy.

As used in this disclosure, one or more scopes can comprise, but are not limited to, one or more microscopes, one or more endoscopes, one or more cameras, and/or one or more instruments used to image (e.g., using optical or other wavelengths, as used in medical imaging systems and/or MBMS). A Multimodality Brain Mapping System (MBMS) according to one or more embodiments of the invention can include, but is not limited to IR, UV, MRI, CT, Ultrasound images, or other images, as well as molecular data, cellular data, genomic data, and patient medical data.

Advantages and Improvements

Benefits of a Multimodality Brain Mapping System (MBMS) (i.e., a System Obtaining IR, UV, MRI, CT, Ultrasound, or Other Images, Image as Well as Molecular, Cellular and Genomic and Patient Medical Data)

Intra-operative magnetic resonance imaging (MRI) and frameless stereotaxis are currently employed as adjuncts to tumor removal. Intra operative MRI suffers from the fact that malignant brain tumors exhibit variable contrast enhancement and therefore portions of the tumor may remain hidden during the surgical procedure. Frameless stereotactic techniques suffer from the inevitability of brain shift, as portions of the tumor are removed during surgery. PET scans cannot be used intraoperatively. Ultrasound, once the resection starts, is limited by signal artifacts caused by blood and surgical trauma at the resection margin [1, 11]. Therefore, there is a pressing need for identifying the margins of an invasive tumor, in order to ensure complete resection. Although fluorescence dyes, time resolved laser induced fluorescence spectroscopy (tr-LIFS), and laser-induced fluorescence of a photosensitizer (hematoporphyrin derivative) have also have been used to delineate various tumors of lung, bladder, colon and brain from the surrounding normal tissue, they have not yet found clinical application for malignant brain tumors [1, 2, 3, 4, 6, 7, 8, 9, 10, 12]. In the specific case of photosensitizers, the photosignaling is dependent on the injection of specific light sensitive compounds. The procedure is invasive and in the case of tr-LIFS, the data acquisition takes a very long time, penetration depth is limited, and the data are only acquired from the very tip of the optical probe. MBMS could use temperature and other gradients on the other hand, due to the change in metabolic pathways in patients with brain tumors, can be detected by IR, UV, or other imaging techniques.

MBMS is a novel technique that has a powerful potential for identifying the margins of intraparenchymal primary and metastatic brain tumors. Previous published data have indicated that metastatic brain tumors, including intracortical melanoma, exhibited hyperthermic profiles [50, 51, 52]. Interestingly, thermography has been used to investigate melanoma and consistently reported that it was hyperthermic. The first experimentation on cutaneous malignant melanoma was conducted in 1964 and revealed a hyperthermic profile with respect to surrounding normal tissue [61]. Subsequent studies revealed similar findings. These studies have established that thermography is a reliable detection and prognostic [85] tool in cutaneous melanoma diagnosis. In addition to the dermatological application of thermal imaging, corneal and ocular malignant melanomas have also been detected using IR thermography. Like cutaneous melanomas and the tumor in [123], these tumors displayed a hyperthermic profile with respect to the surrounding normal tissue [115].

This new modality can provide important real-time imaging information about the tumor location that is not compromised by brain shift, resulting in better intra-operative tumor localization and improving the chance of complete resection. Thus intraoperative use of IR imaging can enable neurosurgeons/medical care providers to more completely delineate brain tumors or other abnormalities such as epileptic regions. Also, in terms of image contrast, new advances in the field of optical imaging and thermoencephalography have made it possible to view the organization of the tissue with respect to its metabolism and blood flow profile. The intraoperative use of an infrared camera can detect the more metabolically active leading edge of the tumor, thereby allowing for a more thorough resection. Previous experimental studies have demonstrated the capability of the infrared imaging technique in enhancing the contrast of human gliomas and tumor margins [1, 7, 8] and can be helpful in identifying remnants of the glioma/abnormalities.

Thus, integration of technology such as MBMS into the operating room of the future can improve the efficiency of tumor resection. Tumor resection has been reported to increase patient survival [120]. Such an improvement would contribute to a higher quality of life for patients, bringing the patients back to the workforce and possibly reducing rehabilitation time and costs, thus making a significant impact on the economical recovery of individuals and the society.

Advantages of the Auto-Delineation System According to One or More Embodiments

Primary and secondary brain tumors affect over 200,000 individuals per year in the United States alone with a high mortality rate and over $49,242 in average direct medical expenses [116, 53]. This does not include rehabilitation costs which will increase dramatically over the years. For patients diagnosed with brain tumors, the likelihood of significant reduction in income increases threefold, since more than ⅔ of them are unable to go back to the workforce [119]. 47% of these patients incur credit card debt, with 7.2% declaring bankruptcy, 15% resorting to a second or third mortgage, and 8.5% caching into their retirement or life insurance savings. Thus, brain tumors put a significant financial strain on the US economy and health care system.

Recent advancements in MRI and CT scan technology offer higher resolution and precision of brain images [107]. However, determination of pre- and post-resection volumes of tumors using MRI are of limited intra-operative value since these scans are typically not performed in real time during the neurosurgery. In most cases, these imaging modalities are still non-dynamic with respect to intra-operative changes of brain topography and tumor dimensions due to intra-operative debulking and manipulations. While the bulk of the tumor can be removed by visual inspection, an accurate visual assessment of tumor margins is extremely difficult because the tumor margins riddled by cancerous cells.

Moreover, existing intraoperative imaging technologies have inherent limitations in providing real-time intraoperative feedback about the completeness of the resection. For example, the use of intraoperative point-by-point biopsy can be time consuming and non-objective, since it is a hit and miss process.

Intraoperative multi-modality imaging can be helpful in resolving these issues, and thus in increasing the extent of resection. One or more embodiments of the invention leverage MBMS in the operating room, both by a real-time visualization of the MBMS image of the brain in alignment with the visible light view, and by employing a tumor auto-delineation software that identifies tumor margins based on the temperature profile of the brain, using modern machine learning techniques. Such delineations can be made available in the real time to the surgeons (neurosurgeons) intraoperatively. Moreover, one embodiments of the invention can assess the margin as well as biological nature of the tumors.

As a result, the auto-delineating system according to one or more embodiments of the invention can lead to complete tumor resection by providing a precise and real time multimodality imaging analysis feedback to neurosurgeons/medical care providers based on ITI, CT, MRI, visible images and biopsy/cellular and or molecular indicators. This system can provide surgeons (e.g., neurosurgeons) with a tool that could dramatically contribute to the surgical precision and intra-operative decision making. This in turn will contribute to lower mortality and morbidity, which could decrease in direct and indirect healthcare costs. Furthermore, the technology can be integrated into the intra-operative microscopes.

In addition, high resolution imaging developed in ultraviolet, visible and near infrared spectral range has wide range of applications in NASA missions as well as commercial and defense applications. However, while the Smart Microscope/endoscope can be used for future Space applications, the immediate benefits include integrating technologies from many different NASA multispecialty groups (e.g., artificial intelligence (AI), mathematical modeling, imaging). This is a clear dual use application of currently existing NASA technologies with significant medical impact on the surgical outcome of complicated brain surgery cases, which could save billions of dollars in healthcare costs in the US alone.

CONCLUSION

This concludes the description of the preferred embodiment of the present invention. The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

REFERENCES

The following references are incorporated by reference herein:

1. Michael M. Haglund et al: Enhanced Optical Imaging of Human Gliomas and Tumor Margins, Neurosurgery, Vol. 38, No. 2, February 1996.
2. Wai S. Poon, et al: Laser-induced fluorescence: experimental intraoperative delineation of tumor resection margins, Journal of Neurosurgery 76:679-86, 1992.
3. Wei-Chiang Lin, Steven A. Toms, Massoud Motamedi, Duco Jansen, Anita-Mandevan-Jansen; Brain Tumor Demarcation using optical spectroscopy; an in vitro study, Journal of Biochemical Optics 5(2), 214-220 (April 2000).
4. Joan K. Frisoli, et. al.; Pharmacokinetics of a Fluorescent Drug Using Laser-Induced Fluorescence, Cancer Research 53, 5954-5961, Dec. 15, 1993
5. Jui Chang Tsai et al; Flurospectral study of the Rat Brain and Glioma in vivo, Laser in Surgery and Medicine 13:321-331 (1993)
6. Reid C. Thompson, M.D., Keith L. Black, M.D., Babek Kateb, Laura Marcu, Ph.D. Time-Resolved Laser-Induced Fluorescence Spectroscopy for detection of Experimental Brain Tumors, Congress of Neurological Surgeons, San Diego, Calif., September 2001 oral/poster presentation
7. Thanassis Papaioannou, Reid C. Thompson, Babak Kateb, Oleg Sorokoumov, Warren S. Grundfest, Keith L. Black: Thermal imaging of brain tumors in a rat glioma model, SPIE proceedings, Vol 4615, Biomedical Diagnostic, Guidance, and Surgical-Assist Systems II, San Jose Calif., 2002. oral/poster presentation
8. Reid Thompson, Thanassis Papaioannov, Babak Kateb, Keith Black; Application of LASER spectroscopy and Thermal Imaging for detection of brain tumors, American Association of Neurological Surgeons, April 2001, Toronto, Canada, abstract/poster
9. Thompson, Reid C.; Black, Keith; Kateb, Babak; Marcu Lura; Detection of experimental brain tumors using time-resolved laser-induced fluorescence spectroscopy, Proc. SPIE Vol. 4613, P. 8-12, Optical Biopsy IV, Robert R. Alfano, Ed, San Jose Calif., 2002
10. Bottiroli G, Croce A C, Locatelli D, Nano R, Giombelli E, Messina A, Benericetti E: Brain tissue autofluorescence: an aid for intraoperative delineation of tumor resection margins. Cancer Detection & Prevention 22:330-339, 1998.
11. Burger P C, Heinz E R, Shibata T, Kleihues P: Topographic anatomy and C T correlations in the untreated glioblastoma multiforme. Journal of Neurosurgery 68:698-704, 1988.
12. Chung Y G, Schwartz J A, Gardner C M, Sawaya R E, Jacques S L: Diagnostic potential of laser-induced autofluorescence emission in brain tissue. Journal of Korean Medical Science 12:135-142, 1997.
13. Tindall G T, Cooper P R, Barrow D L: The Practice of Neurosurgery, William and Wilkins, Volume I, Page 532, 1996
14. Scislowski P W, Slominski A, Bomirski A.: Biochemical characterization of three hamster melanoma variants—II, Glycolysis and oxygen consumption. International Journal of Biochemistry 16(3): 327-31, 1984
15. Halaban R.: Pigmentation in melanomas: changes manifesting underlying oncogenic and metabolic activities. Oncology Research 13(1): 3-8, 2002
16. Lin W C, Toms S A, Motamedi M, Jansen E D, Mahadevan-Jansen A: Brain tumor demarcation using optical spectroscopy; an in vitro study. Journal of Biomedical Optics 5:214-220, 2000.
17. Russ, J C (2002) "The Image Processing Handbook", CRC Press 14. 18. Seul M, O'Gorman L, Sammon M (2001) "Practical Algorithms for Image Analysis", Cambridge University Press
19. Myler H R, Weeks A R (1993) "The Pocket Handbook of Image Processing Algorithms in C", Prentice Hall PTR
20. Comanicu D, Meer P (2002) "Mean shift: A robust approach toward feature space analysis." IEEE Trans. Pattern Anal. Machine Intell., 24, 603-619, May 2002
21. Meer P, Georgescu B (2001) "Edge detection with embedded confidence." IEEE Trans. Pattern Anal. Machine Intell., 23, 1351-1365, December 2001
22. Hertz J, Krogh A, Palmer R G (1991) Introduction to the theory of neural computation, Lecture Notes Volume I, Addison-Wesley Publishing Company
23. Mueller B, Reinhardt J (1990) Neural Networks: An Introduction, Springer, Berlin Heidelberg New York
24. Hopfield J J (1982) Neural Networks and Physical Systems with Emergent collective Computational Abilities, Proc Natl Acad Sci USA 79, 2554
25. Rumelhart D E, Hinton G E, Williams R J (1986) Learning Representations by Back-propagating Errors, Nature 323, 533
26. Rumelhart D E, Hinton G E, Williams R J (1986) Learning Internal Representations by Error Propagation, Parallel Distributed Processing, Vol. 1, Chapter 8, Eds.: Rumelhart D E, McClelland J L, MIT Press, Cambridge
27. Kanter I, Sompolinsky H (1987) Associative Recall of Memory Without Errors, Phys Ref A 35, 380
28. Laws E R, Shaffrey M E, Morris A, Anderson F A Jr: Surgical management of intracranial gliomas—does radical resection improve outcome? Acta Neurochir Suppl 85:47-53, 2003.
29. Brugge J F, Poon P W, So A T, Wu B M, Chan F H, Lam F K. Thermal images of somatic sensory cortex obtained through the skull of rat and gerbil. Exp Brain Res. 1995; 106(1):7-18.
30. George J S, Lewine J D, Goggin A S, Dyer R B, Flynn E R. IR thermal imaging of a monkey's head: local temperature changes in response to somatosensory stimulation. Adv Exp Med Biol. 1993; 333:125-36.
31. J. Zhou, K. L. Chan, V. F. H Chong, S. M. Krishnan, Extraction of brain tumor from MR images using one-class support vector machine, in: IEEE Conf. on Engineering in Medicine and Biology, 2005, pp. 6411-6414.
32. M. Schmidt, I. Levner, R. Greiner, A. Murtha, A. Bistritz, Segmenting brain tumors using alignment-based features, in: IEEE Internat. Conf. on Machine learning and Applications, 2005, pp. 215-220.
33. Lefohn, J. Cates, R. Whitaker, Interactive, GPU-based level sets for 3D brain tumor segmentation, Technical Report, University of Utah, April 2003.
34. Y. Zhu and H. Yang, Computerized tumor boundary detection using a Hopfield neural network, IEEE Transactions on Medical Imaging 16 (1) (1997), pp. 55-67
35. C. Xu and J. L. Prince, "Snakes, Shapes, and Gradient Vector Flow," IEEE Transactions on Image Processing, 7(3), pp. 359-369, March 1998.
36. C. Xu and J. L. Prince, "Gradient Vector Flow: A New External Force for Snakes," Proc. IEEE Conf. on Comp. Vis. Patt. Recog. (CVPR), Los Alamitos: Comp. Soc. Press, pp. 66-71, June 1997.
37. C. Xu and J. L. Prince, "Global Optimality of Gradient Vector Flow", Proc. of 34th Annual Conference on Information Sciences and Systems (CISS '00), Princeton University, March 2000.

38. Li, H. D.; Kallergi, M.; Clarke, L. P.; Jain, V. K.; Clark, R. A., "Markov random field for tumor detection in digital mammography," Medical Imaging, IEEE Transactions on, vol. 14, no. 3, pp. 565-576, September 1995.
39. C-H Lee, M. Schmidt, A. Murtha, A. Bistritz, J. Sander and R. Greiner, "Segmenting Brain Tumors with Conditional Random Fields and Support Vector Machines", Lecture Notes in Computer Science, Volume 3765, 2005.
40. Sturm and Maybank, "On Plane-Based Camera Calibration: A General Algorithm, Singularities, Applications", CVPR99.
41. T. A. Clarke and J. G. Fryer, "The Development of Camera Calibration Methods and Models", Photogrammetric Record, 16(91): 51-66, April 1998.
42. Somayajula S., Joshi A A and Leahy R M, Mutual Information Based Non-Rigid Mouse Registration Using a Scale-space Approach, Proc. of ISBI, pp. 1147-1150, May 2008.
43. Duda, R. O. and Hart, P. E. and Stork, D. G., Pattern Classification, Wiley New York, 2001.
44. Haykin, S., *Neural networks: a comprehensive foundation*, Prentice Hall, 2008.
45. ABTA (American Brain Tumor Association). "Facts & Statistics, 2008" www.abta.org, 2008.
46. Nathoo, N., Toms, S. A., Barnett, G. H., 2004. Metastases to the brain: current management perspectives. Expert Rev. Neurotherapeutics 4 (4), 633-640. 15
47. Tan, T. C., Black, P. M. Image guided craniotomy for cerebral metastases: techniques and outcomes. Neurosurgery 53 (1), 82-90, 2003.
48. Black, P. M., Moriarty, T., Alexander 3rd, E., Stieg, P., Woodard, E. J., Gleason, P. L., Martin, C. H., Kikinis, R., Schwartz, R. B., Jolesz, F. A., 1997b. Development and implementation of intraoperative magnetic resonance imaging and its neurosurgical applications, Neurosurgery 41 (4), 831-842, 2003.
49. Byrne, T. N., Cascino, T. L., Posner, J. B., Brainmetastasis frommelanoma. J. Neuro Oncol., 313-317, 1983.
50. Gorbach, A. M., Infrared imaging of brain function. Adv. Exp. Med. Biol. 333, 95-123, 1993.
51. Gorbach, A. M., Heiss, J. D., Kopylev, L., Oldfield, E. H., Intraoperative infrared imaging of brain tumors, J. Neurosurg. 101, 960-969, 2004.
52. Ecker R D, Goerrss S J, Meyer F B, Cohen-Gadol A A, Britton J W and Levine J A, Vision of the future: Initial Experience with Real-time Intraoperative High-Resolution Dynamic Infrared Imaging (DIRI), Journal of Neurosurgery 97 (6): 1460-71, (2002).
53. ABTA (American Brain Tumor Association). "Facts & Statistics, 2008" www.abta.org
54. Arora N, Martins D, Ruggerio D, Tousimis E, Swistel A J, Osborne M P, Simmons R M. Am J Surg., Effectiveness of a noninvasive digital infrared thermal imaging system in the detection of breast cancer.196(4):523-6, 2008.
55. Barrett A H, Myers P C, and Sadowsky N L. Microwave Thermography in the Detection of Breast Cancer. AJR, Am J Roengenol. 34(2); 365-368, (1980).
56. Black P, Moriarty T, Alexander E, et al. Development and implementation of intraoperative magnetic resonance imaging and its neurosurgical applications. Neurosurgery.; 41:831-845, (1997).
57. Black P M, Moriarty T, Alexander E 3rd, Stieg P, Woodard E J, Gleason P L, Martin C H, Kikinis R, Schwartz R B, Jolesz F A, Development and implementation of intraoperative magnetic resonance imaging and its neurosurgical applications. Neurosurgery; 41(4): 831-42, (1997).
58. Burger P C, Heinz E R, Shibata T, Kleihues P, Topographic anatomy and C T correlations in the untreated glioblastoma multiforme. Journal of Neurosurgery 68:698-704, (1988).
59. Byrne T N, Cascino T L, and Posner J B, Brain Metastasis from Melanoma. Journal of Neuro-Oncology, 1:313-317, (1983).
60. DeAngelis L M. Brain tumors, N Engl J Med; 344:114-23, (2001).
61. Di Carlo A: Thermography and the possibilities for its applications in clinical and experimental dermatology. Clinics in Dermatology 13:329-336, (1995).
62. Ecker R D, Goerrss S J, Meyer F B, Cohen-Gadol A A, Britton J W and Levine J A, Vision of the future: Initial Experience with Real-time Intraoperative High-Resolution Dynamic Infrared Imaging (DIRI), Journal of Neurosurgery 97 (6): 1460-71, (2002).
63. Fahlbusch R and Samii A, A Review of Cranial Imaging Techniques: Potential and Limitations, Clinical Neurosurgery, The Congress of Neurological Surgeons, Vol. 54, ch 17, 100-104, (2007).
64. Frangioni J V. New technologies for human cancer imaging J Clin Oncol. 26(24):4012-21, (2008).
65. Gonzalez, Francisco Javier. Infrared Imager Requirements for Breast Cancer Detection. Proceedings of the 29th Annual Int'l Conference of the IEEE EMBS. 3312-3314, (2007).
66. Gorbach A, Simonton D, Hale D A, Swanson S J, Kirk A D. Objective, real-time, intraoperative assessment of renal perfusion using infrared imaging. Am J Transplant.; 3(8):988-93, (2003).
67. Gorbach A M, Wang H, Dhanani N N, Gage F A, Pinto P A, Smith P D, Kirk A D, Elster E A., Assessment of critical renal ischemia with real-time infrared imaging. J Surg Res.149(2):310-8, (2008).
68. Gorbach A M, Infrared imaging of brain function. Advances in Experimental Medicine & Biology 333:95-123, (1993).
69. Gorbach, A M, Heiss, J D, Kopylev, L and Oldfield, E H, Intraoperative infrared imaging of brain tumors, J Neurosurg 101:960-969, (2004).
70. Hadani M, Spiegelman R, Feldman Z, et al. Novel, compact, intraoperative magnetic resonance imaging-guided system for conventional neurosurgical operating rooms. Neurosurgery.; 48: 799-809, (2001).
71. Hall W, Liu H, Martin A J, et al. Safety, efficacy, and functionality of high-field strength interventional magnetic resonance imaging for neurosurgery. Neurosurgery.; 46:632-642, (2000).
72. Hall W A, Truwit C L. Intraoperative MR-guided neurosurgery. J Magn Reson Imaging. February; 27(2):368-75, (2008).
73. Head J F, Wang F, Lipari C A and Elliot R L., The Important Role of Infrared Imaging in Breast Cancer. IEEE Eng Med Biol Mag. 19(2) 52-57, (2000).
74. Hill, D; Maurer, C; Maciunas, R; Barwise, J; Fitzpatrick, J; Wang, M., Measurement of intraoperative brain surface deformation under a craniotomy. Neurosurgery.43(3): 514-26, (1998) 16
75. Holland B A, Brant-Zawadzki M, Norman D, Newton T H: Magnetic resonance imaging of primary intracranial tumors: a review. International Journal of Radiation Oncology, Biology, Physics 11:315-321, (1985).
76. Jiang L J, Ng E Y, Yeo A C, Wu S, Pan F, Yau W Y, Chen J H, Yang Y., a perspective on medical infrared imaging. J Med Eng Technol. 29 (6):257-67, (2005).

77. Knauth, M; Wirtz, C; Tronnier, V; Aras, N; Kunze, S; Sartor, K., Intraoperative MR imaging increases the extent of tumor resection in patients with high-grade gliomas. Am J Neuroradiology. (9):1642-6, (1999).
78. Kelly P J, Daumas-Duport C, Scheithauer B W, Kall B A, Kispert D B, Stereotactic histologic correlations of computed tomography- and magnetic resonance imaging-defined abnormalities in patients with glial neoplasms. Mayo Clinic Proceeding 62:450-459, (1987).
79. Konerding M A, Konerding M A, Fait E, Dimitropoulou C, Malkusch W, Ferri C, Giavazzi R, Coltrini D, Presta M., Impact of fibroblast growth factor-2 on tumor microvascular architecture. A tridimensional morphometric study. Am J Pathol.152(6):1607-16, (1998).
80. Laws E R, Shaffrey M E, Morris A, Anderson F A Jr: Surgical management of intracranial gliomas—does radical resection improve outcome? Acta Neurochir Suppl 85:47-53, (2003).
81. Lindner D, Trantakis C, Renner C, Arnold S, Schmitgen A, Schneider J, Meixensberger J., Application of intraoperative 3D ultrasound during navigated tumor resection, Minim Invasive Neurosurg.; 49(4):197-202, (2006).
82. McCulloch J.: Perivascular nerve fibres and the cerebral circulation. Trends in Neurosciences 7:135-138, (1984).
83. McGirt M J, Chaichana K L, Gathinji M, Attenello F J, Than K, Olivi A, Weingart J D, Brem H, Quinones-Hinojosa A R., Independent association of extent of resection with survival in patients with malignant brain astrocytoma, J Neurosurg. January; 110(1):156-62, (2009).
84. Merla, A.; Romani, G. L., Functional Infrared Imaging in Medicine: A Quantitative Diagnostic Approach Conf Proc IEEE Eng Med Biol Soc. 1:224-7, (2006).
85. Michel U, Hornstein O P, Schonberger A., Infrared thermography in malignant melanoma. Diagnostic potential and limits [in German]. Hautarzt 36:83-89, (1985).
86. Mineo J F, Quintin-Roue I, Lucas B, Buburusan V, Besson G, Glioblastomas: clinical study and search for prognostic factors [in French]. Neurochirurgie 48:500-509, (2002).
87. Mital M and Scott E P, Thermal Detection of Embedded Tumors Using Infrared Imaging. J Biomech Eng. (129) 33-39, (2007).
88. Mitchell P, Ellison D W, and Mendelow A D, Surgery for Malignant Gliomas: Mechanistic Reasoning and Slippery Statistics. Lancet Neurology, 4: 413-422, (2005).
89. Mittal S and Black P M Intraoperative magnetic resonance imaging in neurosurgery: the Brigham concept. Acta Neurochir Suppl. 2006; 98:77-86, (2006).
90. Nabavi A, Black P M, Gering D T, Westin C F, Mehta V, Pergolizzi R S Jr, Ferrant M, Warfield S K, Hata N, Schwartz R B, Wells W M 3rd, Kikinis R, Jolesz F A, Serial intraoperative magnetic resonance imaging of brain shift. Neurosurgery.48(4):787-97, (2001).
91. Nakagawa A, Fujimura M, Arafune T, Sakuma I, Tominaga T, Intraoperative infrared brain surface blood flow monitoring during superficial temporal artery-middle cerebral artery anastomosis in patients with childhood moyamoya disease. Childs Nery Syst.; 24(11): 1299-305, (2008).
92. Nakao N, Nakai K, Itakura T, Updating of neuronavigation based on images intraoperatively acquired with a mobile computerized tomographic scanner: technical note, Minim Invasive Neurosurg; 46(2):117-20, (2003).
93. Nathoo N, Toms S A, and Barnett G H, Metastases to the brain: current management perspectives. Expert Rev Neurotherapeutics. 4(4): 633-640, (2004).
94. Nazzaro J M, Neuwelt E A, The role of surgery in the management of supratentorial intermediate and high-grade astrocytomas in adults. Journal of Neurosurgery 73:331-344, (1990).
95. Nishikawa K, Matsudaira H, Suzuki H, Mizuno R, Hanyuu N, Iwabuchi S, Yanaga K. Intraoperative thermal imaging in esophageal replacement: its use in the assessment of gastric tube viability. Surg Today.; 36(9):802-6, (2006).
96. Papaioannou T, Thompson R C, Kateb B, Sorokoumov O, Grundfest W S, Black K L, Thermal imaging of brain tumors in a rat glioma model, Proc. SPIE, Vol. 4615, 32; DOI:10.1117/12.466653, (2002).
97. Rasmussen I A, Lindseth F, Rygh O M, Berntsen E M, Selbekk T, Xu J, Nagelhus Hernes T A, Harg E, Haberg A, and Unsgaard G., Functional neuronavigation combined with intra-operative 3D ultrasound: Initial 17 experiences during surgical resections close to eloquent brain areas and future directons in automatic brain shift compensation of preoperative data. Acta Neurochir; 149: 365-378, (2007).
98. Reinertsen I, Descoteaux M, Siddiqi K, Collins D L., Validation of vessel-based registration for correction of brain shift. Med Image Anal. 11(4):374-88, (2007).
99. Samaras C A and Greenblatt R B, The role of Thermography in Breast Cancer, Contemp Surg 22:31-38, (1983).
100. Sanai N and Berger M S, Glioma Extent of Resection and Its Impact on Patient Outcome. Neurosurgery; 62 (4); 753-766, (2008).
101. Saxena A K and Willital G H, Infrared Thermography: Experience from a decade of Pediatric Imaging. Eur J Pediatr. 167: 757-764, (2008).
102. Schulder M, Liang D, Carmel P W. Cranial surgery navigation aided by a compact intraoperative magnetic resonance imager. J Neurosurg.; 94:936-945, (2001).
103. Schulder, M, and Carmel, P W Intraoperative Magnetic Resonance Imaging: Impact on Brain Tumor Surgery, Cancer Control 10(2):115-124, (2003).
104. Shevelev I A, Tsicalov E N, Gorbach A M, Budko K P, and Sharaev G A, Thermoimaging of the brain, Journal of Neuroscience Methods, 46-49-57, (1993).
105. Shevelev I A Functional imaging of the brain by infrared radiation (thermoencephaloscopy). Progress in Neurobiology 56:269-305, (1998).
106. Shevelev I A Temperature topography of the brain cortex: thermoencephaloscopy. Brain Topography 5:77-85, (1992).
107. Shi W M, Wildrick D M, Sawaya R, Volumetric measurement of brain tumors from MR imaging. Journal of Neuro-Oncology 37:87-93, (1993).
108. Stupp R, Mason W P et al, Radiotherapy plus Concomitant and Adjuvant Temozolomide for Glioblastoma; N Engl J Med. (10):987-96, (2006).
109. Tan T C and Black P M, Image-Guided Craniotomy for Cerebral Metastases: Techniques and Outcomes. Neurosurgery 53 (1): 82-90 (2003).
110. Tempany C; McNeil B Advances in Biomedical Imaging. JAMA; 285(5):562-567, (2001).
111. Unsgaard G, Rygh O M, Selbekk T, Müller T B, Kolstad F, Lindseth F, Hernes T A Acta Neurochir; 148(3):235-53, (2006).
112. Ueda M, Sakurai T, Kasai K, Ushikubo Y, and Samejima H, Localisation of Sensory Motor Cortex During Surgery by Changes of Cortical Surface Temperature after Median Nerve Stimulation. The Lancet. Vol 350; 9077: p561, (1997).
113. Watson J C, Gorbach A M, Pluta R M, Rak R, Heiss J D, Oldfield E H, Real-time detection of vascular occlusion and reperfusion of the brain during surgery by using infrared imaging. Journal of Neurosurgery 96:918-923, (2002).
114. Wen P Y, Kesari S, Malignant gliomas in adults, N Engl J Med. (5):492-507, (2008).
115. Wittig I, Kohlmann H, Lommatzsch P K, Kruger L, Herold H, Static and dynamic infrared thermometry and thermography in malignant melanoma of the uvea and conjunctiva [in German]. Klinische Monatsblatter fur Augenheilkunde 201:317-321, (2002).
116. L. Kutikova, L. Bowman, S. Chang and S. Long, How costly is brain cancer? Healthcare services use and costs from across the US, Journal of Clinical Oncology, 2004 ASCO Annual Meeting Proceedings, Vol 22(14S) (2004).
117. Maintz, J. B. A. and Viergever, M. A., A survey of medical image registration, Medical image analysis, Vol 2(1), pp. 1-36, (1998).
118. Maes, F., Collignon, A., Vandermeulen, D., Marchal, G. and Suetens, P., Multimodality image registration by maximization of mutual information, IEEE trans. on Medical Imaging, Vol 16 (2), pp. 187-198, (1997).
119. Patterson, H., Nobody can Afford a Brain Tumor: The Financial Impact of Brain Tumors on Patients and Families. A Summary Finding, NBT Foundation San Francisco, Calif., 2007.
120. Murphy, M., Dinsmore, J., Wilkins, P R and Marsh, H T., Preuss Resident Research Award: maximal resection of low-grade intrinsic brain tumors using "awake" craniotomy and multiple marginal smear biopsies: neurological deficit rate and long-term survival data, Clinical neurosurgery, Vol 53, pp332, (2006).
121. Hermann B. Frieboes, John S. Lowengrub, S. Wise, X. Zheng, Paul Macklin, Elaine L. Bearer, and Vittorio Cristini, Computer simulation of glioma growth and morphology, Neuroimage 37 (2007) S59-S70.
122. Sandeep Sanga, Hermann B. Frieboes, Xiaoming Zheng, Robert Gatenby, Elaine L. Bearer, and Vittorio Cristini, Predictive oncology: A review of multidisciplinary, multiscale in silico modeling linking phenotype, morphology and growth, NeuroImage 37 (2007) S120-S134.
123. Babak Kateb, Vicky Yamamoto Cheng Yu, Warren Gr Hest, John Peter Gruen, Infrared thermal imaging: A review of the literature and case report, Neuroimage 47 (2009) T154-T162.

What is claimed is:

1. A system, comprising one or more scopes coupled to one or more processors, wherein:
the one or more processors:
obtain training data from one or more first images and/or first data, wherein one or more abnormal regions and one or more normal regions are identified;
receive a second image captured by one or more of the scopes at a later time than the one or more first images and/or first data and/or captured using a different imaging technique; and
generate, using machine learning trained using the training data, one or more viewable indicators identifying one or more abnormalities in the second image, wherein the one or more viewable indicators are generated in real time as the second image is formed; and
one or more of the scopes display the one or more viewable indicators on the second image.

2. The system of claim 1, wherein:
one or more of the processors comprise one or more multi-modality data processors; and
the multi-modality data processors register at least two of the first images and/or first data obtained from biopsy, Infrared Imaging, Ultraviolet Imaging, Diffusion Tensor Imaging (DTI), Computed Tomography (CT), Magnetic Resonance Imaging (MRI), Brain Mapping Ultrasound, cellular data, molecular data, genomic data, optical imaging, and Functional MRI (FMRI), to form a registered image and/or patient data; and
one or more of the processors receive input that identifies or marks the one or more abnormal and one or more normal regions in the registered image and/or patient data.

3. The system of claim 1, wherein the one or more first images comprise a pre-operative image, an intra-operative image, and/or a post operative image of one or more patients.

4. The system of claim 1, wherein:
the one or more scopes comprise one or more first scopes and a second scope; and
the one or more first scopes capture the one or more first images of one or more patients and the second scope captures the second image of a different patient.

5. The system of claim 4, further comprising:
a cloud and/or parallel computing system wherein the training data obtained from the one or more first images captured in the one or more first scopes is shared so that the machine learning learns from the training data to identify the one or more abnormalities in the second image of the different patient.

6. The system of claim 1, wherein the processors that predict growth of the one or more abnormalities in the second image from predictive modeling of, and/or pattern recognition in, the training data.

7. The system of claim 1, wherein one or more of the processors:
represent the one or more abnormal regions with first feature vectors defining first coordinates in a feature space;
represent the one or more normal regions with second feature vectors defining second coordinates in the feature space, wherein the feature space is selected such that at least some of the first coordinates and at least some of the second coordinates are on opposite sides of a hyper-plane in the feature space;
map an image region of the second image to one or more image coordinates in the feature space;
classify one or more of the image coordinates as one or more abnormal coordinates depending on one or more factors, including:
which side of the hyper-plane the one or more image coordinates lie; and/or
proximity of the one or more image coordinates to the first coordinates and/or the hyper-plane; and
indicate the image region as an abnormal image region if the image region is mapped to one or more of the abnormal coordinates according to the map.

8. The system of claim 1, wherein the one or more processors implement a support vector machine.

9. The system of claim 1, wherein:
one or more of the scopes comprise one or more microscopes and/or one or more endoscopes including an optical imaging system for capturing the second image; and
the second image comprises an optical image.

10. The system of claim 1, wherein:
one or more of the one or more scopes comprise a surgical scope capturing the second image during a surgical procedure on a patient, and
the one or more viewable indicators enable the one or more abnormalities to be surgically removed from the patient, during the surgical procedure, with increased precision by reducing damage to normal tissue.

11. A method for identifying one or more abnormalities in an image, comprising:
obtaining training data from one or more first images and/or first data, wherein one or more abnormal regions and one or more normal regions in the one or more first images and/or first data are identified;
receiving a second image of the tissue captured at a later time than the one or more first images and/or first data and/or using a different imaging technique; and
generating, using machine learning trained using the training data, one or more viewable indicators identifying one or more abnormalities in the second image, wherein the one or more viewable indicators are generated in real time as the second image is formed.

12. The method of claim 11, further comprising:
registering at least two of the first images and/or first data obtained from biopsy, Infrared Imaging, Ultraviolet Imaging Diffusion Tensor Imaging (DTI), Computed Tomography (CT), Magnetic Resonance Imaging (MRI), Brain Mapping Ultrasound, cellular data, molecular data, and genomic data, optical imaging, and Functional MRI (FMRI), to form a registered image and/or patient data; and
receiving input that identifies or marks the one or more abnormal and one or more normal regions in the registered image and/or patient data.

13. The method of claim 12, wherein the one or more first images comprise a pre-operative image and/or a post operative image of a patient.

14. The method claim 11, further comprising:
obtaining the one or more first images of one or more patients captured with one or more first scopes; and
obtaining the second image of a different patient captured with a second scope.

15. The method of claim 14, further comprising connecting the one or more first scope and the second scope using a cloud and/or parallel computing system wherein the training data obtained from the one or more first images captured in the one or more first scopes is shared so that the machine learning learns from the training data to identify the one or more abnormalities in the second image of the different patient.

16. The method of claim 11, wherein the machine learning predicts growth of the one or more abnormal cells in the second image from predictive modeling of, and/or pattern recognition in, the training data.

17. The method of claim 11, further comprising:
representing the one or more abnormal regions with first feature vectors defining first coordinates in a feature space;
representing the one or more normal regions with second feature vectors defining second coordinates in the feature space, wherein the feature space is selected such that at least some of the first coordinates and at least some of the second coordinates are on opposite sides of a hyper-plane in the feature space;
mapping an image region of the second image to one or more image coordinates in the feature space;
classifying one or more of the image coordinates as one or more abnormal coordinates depending on one or more factors, including:
which side of the hyper-plane the one or more image coordinates lie; and/or
proximity of the one or more image coordinates to the first coordinates and/or the hyper-plane; and
indicating the image region as an abnormal image region if the image region is mapped to one or more of the abnormal coordinates according to the mapping.

18. The method of claim 11, wherein the machine learning comprises a support vector machine.

19. The method of claim 11, wherein:
the second image comprises an optical image captured during a surgical procedure on a patient, and
the one or more viewable indicators enable the one or more abnormalities to be surgically removed from the patient, during the surgical procedure, with increased precision by reducing damage to non-cancerous tissue.

20. The method of claim 11, further comprising capturing the second image with a microscope, endoscope, and/or camera.

* * * * *